(12) United States Patent
Eis et al.

(10) Patent No.: US 9,777,004 B2
(45) Date of Patent: Oct. 3, 2017

(54) AMINO-SUBSTITUTED IMIDAZOPYRIDAZINES

(71) Applicant: Bayer Intellectual Property GmbH, Monheim (DE)

(72) Inventors: Knut Eis, Berlin (DE); Florian Puehler, Wellesley, MA (US); Ludwig Zorn, Berlin (DE); Volker Schulze, OT Bergf (DE); Detlev Sülzle, Berlin (DE); Philip Lienau, Berlin (DE); Andrea Hägebarth, Berlin (DE); Kirstin Petersen, Berlin (DE); Ulf Bömer, Glienicke (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/388,940

(22) PCT Filed: Mar. 27, 2013

(86) PCT No.: PCT/EP2013/056488
§ 371 (c)(1),
(2) Date: Sep. 29, 2014

(87) PCT Pub. No.: WO2013/144189
PCT Pub. Date: Oct. 3, 2013

(65) Prior Publication Data
US 2015/0087631 A1    Mar. 26, 2015

(30) Foreign Application Priority Data
Mar. 29, 2012    (EP) .................................... 12162037

(51) Int. Cl.
C07D 487/04    (2006.01)
A61K 31/5025   (2006.01)
A61K 31/5377   (2006.01)

(52) U.S. Cl.
CPC ........ C07D 487/04 (2013.01); A61K 31/5025 (2013.01); A61K 31/5377 (2013.01)

(58) Field of Classification Search
CPC ................................................. C07D 49/1048
See application file for complete search history.

(56) References Cited

U.S. PATENT DOCUMENTS

| | | | |
|---|---|---|---|
| 9,284,319 B2 | 3/2016 | Eis et al. | |
| 9,320,737 B2 | 4/2016 | Eis et al. | |
| 9,409,889 B2 | 8/2016 | Eis et al. | |
| 9,499,547 B2 | 11/2016 | Kong et al. | |
| 2007/0093490 A1 | 4/2007 | Prien et al. | |
| 2009/0093475 A1 | 4/2009 | Prien et al. | |
| 2014/0194430 A1 | 7/2014 | Eis et al. | |
| 2014/0228370 A1 | 8/2014 | Eis et al. | |
| 2014/0288069 A1 | 9/2014 | Eis et al. | |
| 2014/0296231 A1 | 10/2014 | Eis et al. | |
| 2014/0364435 A1 | 12/2014 | Eis et al. | |
| 2015/0038485 A1 | 2/2015 | Eis et al. | |
| 2015/0094300 A1 | 4/2015 | Eis et al. | |
| 2015/0291599 A1 | 10/2015 | Zorn et al. | |
| 2015/0376189 A1 | 12/2015 | Zorn et al. | |
| 2016/0287589 A1 | 10/2016 | Fis et al. | |
| 2017/0029441 A1 | 2/2017 | Schulze et al. | |

FOREIGN PATENT DOCUMENTS

| | | |
|---|---|---|
| WO | WO 2007/013673 | 2/2007 |
| WO | WO 2007/025090 | 3/2007 |
| WO | WO 2007/147646 | * 6/2007 |
| WO | WO 2007/147646 | 12/2007 |
| WO | WO 2008/025822 | 3/2008 |
| WO | WO 2009/086130 | 7/2009 |
| WO | WO 2012/156367 | 11/2012 |
| WO | WO 2012/175591 | 12/2012 |
| WO | WO 2013/034570 | 3/2013 |

(Continued)

OTHER PUBLICATIONS

Vippagunta et al. (2001).*
U.S. Appl. No. 14/118,519, filed May 7, 2014.*
U.S. Appl. No. 14/118,519, filed Feb. 5, 2014.*
U.S. Appl. No. 14/118,519, filed Jun. 10, 2014.*
International Preliminary Report on Patentability and Written Opinion from PCT with Issuance Date of Oct. 1, 2014 in connection with International Application No. PCT/EP/2013/056488; 7 pages.

(Continued)

*Primary Examiner* — Paul V Ward
(74) *Attorney, Agent, or Firm* — Nixon & Vanderhye P.C.

(57) ABSTRACT

The present invention relates to amino-substituted imidazopyridazine compounds of general formula (I), in which A, R1, R2, R3, R4, R5 and n are as defined in the claims, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

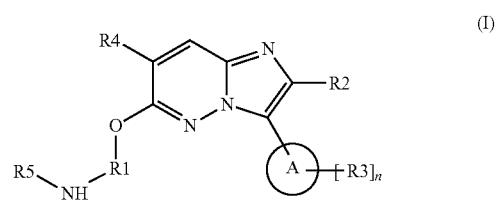

9 Claims, No Drawings

(56) References Cited

FOREIGN PATENT DOCUMENTS

WO    WO 2013/041634    3/2013

OTHER PUBLICATIONS

International Search Report from PCT with Date of Mailing of May 15, 2013 in connection with the International Application No. PCT/EP2013/056488; 4 pages.
Oyarzabal et al., "Discovery of Mitogen-Activated Protein Kinase-Interacting Kinase 1 Inhibitors by a Comprehensive Fragment-Oriented Virtual Screening Approach", *Journal of Medicinal Chemistry*, (2010), vol. 53, No. 18, pp. 6618-6628.

\* cited by examiner

AMINO-SUBSTITUTED IMIDAZOPYRIDAZINES

The present invention relates to amino-substituted imidazopyridazine compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

BACKGROUND OF THE INVENTION

The present invention relates to chemical compounds that inhibit MKNK1 kinase (also known as MAP Kinase interacting Kinase, Mnk1) and MKNK2 kinase (also known as MAP Kinase interacting Kinase, Mnk2). Human MKNKs comprise a group of four proteins encoded by two genes (Gene symbols: MKNK1 and MKNK2) by alternative splicing. The b-forms lack a MAP kinase-binding domain situated at the C-terminus. The catalytic domains of the MKNK1 and MKNK2 are very similar and contain a unique DFD (Asp-Phe-Asp) motif in subdomain VII, which usually is DFG (Asp-Phe-Gly) in other protein kinases and suggested to alter ATP binding [Jauch et al., Structure 13, 1559-1568, 2005 and Jauch et al., EMBO J25, 4020-4032, 2006]. MKNK1a binds to and is activated by ERK and p38 MAP Kinases, but not by JNK1. MKNK2a binds to and is activated only by ERK. MKNK1 b has low activity under all conditions and MKNK2b has a basal activity independent of ERK or p38 MAP Kinase. [Buxade M et al., Frontiers in Bioscience 5359-5374, May 1, 2008]

MKNKs have been shown to phosphorylate eukaryotic initiation factor 4E (eIF4E), heterogeneous nuclear RNA-binding protein A1 (hnRNP A1), polypyrimidine-tract binding protein-associated splicing factor (PSF), cytoplasmic phospholipase A2 (cPLA2) and Sprouty 2 (hSPRY2) [Buxade M et al., Frontiers in Bioscience 5359-5374, May 1, 2008].

eIF4E is an oncogene that is amplified in many cancers and is phosphorylated exclusively by MKNKs proteins as shown by KO-mouse studies [Konicek et al., Cell Cycle 7:16, 2466-2471, 2008; Ueda et al., Mol Cell Biol 24, 6539-6549, 2004]. eIF4E has a pivotal role in enabling the translation of cellular mRNAs. eIF4E binds the 7-methylguanosine cap at the 5' end of cellular mRNAs and delivers them to the ribosome as part of the eIF4F complex, also containing eIF4G and eIF4A. Though all capped mRNAs require eIF4E for translation, a pool of mRNAs is exceptionally dependent on elevated eIF4E activity for translation. These so-called "weak mRNAs" are usually less efficiently translated due to their long and complex 5' UTR region and they encode proteins that play significant roles in all aspects of malignancy including VEGF, FGF-2, c-Myc, cyclin D1, survivin, BCL-2, MCL-1, MMP-9, heparanase, etc. Expression and function of eIF4E is elevated in multiple human cancers and directly related to disease progression [Konicek et al., Cell Cycle 7:16, 2466-2471, 2008].

MKNK1 and MKNK2 are the only kinases known to phosphorylate eIF4E at Ser209. Overall translation rates are not affected by eIF4E phosphorylation, but it has been suggested that eIF4E phosphorylation contributes to polysome formation (i.e. multiple ribosome on a single mRNA) that ultimately enables more efficient translation of "weak mRNAs" [Buxade M et al., Frontiers in Bioscience 5359-5374, May 1, 2008]. Alternatively, phosphorylation of eIF4E by MKNK proteins might facilitate eIF4E release from the 5' cap so that the 48S complex can move along the "weak mRNA" in order to locate the start codon [Blagden S P and Willis A E, Nat Rev Clin Oncol. 8(5):280-91, 2011]. Accordingly, increased eIF4E phosphorylation predicts poor prognosis in non-small cell lung cancer patients [Yoshizawa et al., Clin Cancer Res. 16(1):240-8, 2010]. Further data point to a functional role of MKNK1 in carcinogenesis, as overexpression of constitutively active MKNK1, but not of kinase-dead MKNK1, in mouse embryo fibroblasts accelerates tumor formation [Chrestensen C. A. et al., Genes Cells 12, 1133-1140, 2007]. Moreover, increased phosphorylation and activity of MKNK proteins correlate with overexpression of HER2 in breast cancer [Chrestensen, C. A. et al., J. Biol. Chem. 282, 4243-4252, 2007]. Constitutively active, but not kinase-dead, MKNK1 also accelerated tumor growth in a model using Eµ-Myc transgenic hematopoietic stem cells to produce tumors in mice. Comparable results were achieved, when an eIF4E carrying a S209D mutation was analyzed. The S209D mutation mimicks a phosphorylation at the MKNK1 phosphorylation site. In contrast a non-phosphorylatable form of eIF4E attenuated tumor growth [Wendel H G, et al., Genes Dev. 21(24):3232-7, 2007]. A selective MKNK inhibitor that blocks eIF4E phosphorylation induces apoptosis and suppresses proliferation and soft agar growth of cancer cells in vitro. This inhibitor also suppresses outgrowth of experimental B16 melanoma pulmonary metastases and growth of subcutaneous HCT116 colon carcinoma xenograft tumors without affecting body weight [Konicek et al., Cancer Res. 71(5):1849-57, 2011]. In summary, eIF4E phosphorylation through MKNK protein activity can promote cellular proliferation and survival and is critical for malignant transformation. Inhibition of MKNK activity may provide a tractable cancer therapeutic approach.

WO 2007/025540 A2 (Bayer Schering Pharma AG) relates to substituted imidazo[1,2-b]pyridazines as kinase inhibitors, particularly PKC (protein kinase C) inhibitors, in particular PKC theta inhibitors.

WO 2007/025090 A2 (Kalypsis, Inc.) relates to heterocyclic compounds useful as inhibitors of Mitogen-activated protein kinase (MAPK)/Extracellular signal-regulated protein kinase (Erk) Kinase (abbreviated to "MEK"). In particular, WO 2007/025090 A2 relates inter alia to imidazo[1,2-b]pyridazines.

WO 2007/013673 A1 (Astellas Pharma Inc.) relates to fused heterocycles as inhibitors of Lymphocyte protein tyrosine kinase (abbreviated to "LCK"). In particular, WO 2007/013673 A1 relates inter alia to imidazo[1,2-b]pyridazines.

WO 2007/147646 A1 (Bayer Schering Pharma AG) relates to oxo-substituted imidazo[1,2-b]pyridazines as kinase inhibitors, particularly PKC (protein kinase C) inhibitors, in particular PKC theta inhibitors.

WO 2008/025822 A1 (Cellzome (UK) Ltd.) relates to diazolodiazine derivatives as kinase inhibitors. In particular, WO 2008/025822 A1 relates inter alia to imidazo[1,2-b]pyridazines as kinase inhibitors, particularly inducible T cell kinase (abbreviated to "Itk") inhibitors.

WO 2008/030579 A2 (Biogen Idec MA Inc.) relates to modulators of interleukin-1 (IL-1) receptor-associated kinase (abbreviated to "IRAK"). In particular, WO 2008/030579 A2 relates inter alia to imidazo[1,2-b]pyridazines.

WO 2008/058126 A2 (Supergen, Inc.) relates inter alia to imidazo[1,2-b]pyridazine derivatives as protein kinase inhibitors, particularly PIM kinase inhibitors.

WO 2009/060197 A1 (Centro Nacional de Investigaciones Oncologicas (CNIO)) relates to imidazopyridazines as protein kinase inhibitors, such as the PIM family kinases.

U.S. Pat. No. 4,408,047 (Merck & Co., Inc.,) relates inter alia to imidazopyridazines having a 3-amino-2-OR-propoxy substituent having beta-adrenergic blocking activity.

WO 03/018020 A1 (Takeda Chemical Industries, Ltd.) relates to inhibitors against c-Jun N-terminal kinase, containing compounds which are, inter alia, imidazo[1,2-b]-pyridazines.

WO 2008/052734 A1 (Novartis AG) relates to heterocyclic compounds as antiinflammatory agents. In particular said compounds are, inter alia, imidazo[1,2-b]pyridazines. The compounds are useful for treating diseases mediated by the ALK-5 and/or ALK-4 receptor, and are also useful for treating diseases mediated by the PI3K receptor, the JAK-2 receptor and the TRK receptor.

WO 2008/072682 A1 (Daiichi Sankyo Company, Limited) relate to imidazo[1,2-b]pyridazine derivative which has an action of inhibiting TNF-alpha production, exerts an effect in a pathological model of inflammatory disease and/or auto-immune disease.

WO 2008/079880 A1 (Alcon Research, Ltd.) relates to 6-aminoimidazo[1,2-b]pyridazine analogues as Rho-kinase inhibitors for the treatment of glaucoma and ocular hypertension.

WO 2009/091374 A2 (Amgen Inc.) relates to fused heterocyclic derivatives. Selected compounds are effective for prophylaxis and treatment of diseases, such as hepatocyte growth factor ("HGF") diseases.

In J. Med. Chem., 2005, 48, 7604-7614, is an article entitled "Structural Basis of Inhibitor Specificity of the Protooncogene Proviral Insertion Site in Moloney Murine Leukemia Virus (PIM-1) Kinase", and discloses, inter alia, imidazo[1,2-b]pyridazines as inhibitor structures used in the study described therein.

In J. Med. Chem., 2010, 53, 6618-6628, is an article entitled "Discovery of Mitogen-Activated Protein Kinase-Interacting Kinase 1 Inhibitors by a Comprehensive Fragment-Oriented Virtual Screening Approach", and discloses, inter alia, in Table 1., some specific imidazo[1,2-b] pyridazines as compounds identified as MKNK-1 inhibitors.

In Cancer Res Mar. 1, 2011, 71, 1849-1857 is an article entitled "Therapeutic inhibition of MAP kinase interacting kinase blocks eukaryotic initiation factor 4E phosphorylation and suppresses outgrowth of experimental lung mestastases", and discloses, inter alia, that the known antigfungal agent Cercosporamide is an inhibitor of MKNK1.

However, the state of the art described above does not describe the specific substituted imidazopyridazine compounds of general formula (I) of the present invention as defined herein, i.e. an imidazo[1,2-b]pyridazinyl moiety, bearing:

in its 3-position, a:

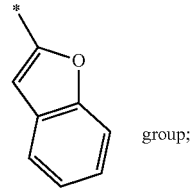 [SMILES: *c1cc2ccccc2o1]

group;

in its 6-position, a group of structure:

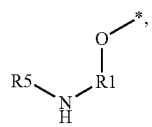

wherein:
* indicates the point of attachment of said group with the rest of the molecule,
R1 represents a linear $C_1$-$C_6$-alkyl-, a branched $C_3$-$C_6$-alkyl-, or a $C_3$-$C_6$-cycloalkyl-group which is optionally substituted as defined herein, and
R5 represents:
either:
a substituent as defined herein;
or:
together, with the nitrogen atom to which it is bound, and with a carbon atom of R1, form a 3- to 7-membered cyclic secondary amine group as defined herein;
or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit MKNK-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

DESCRIPTION OF THE INVENTION

In accordance with a first aspect, the present invention covers compounds of general formula (I):

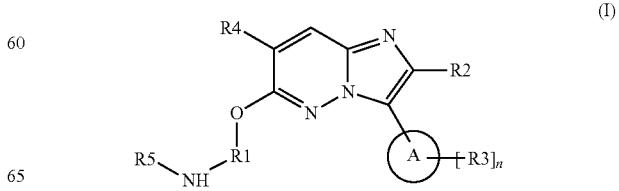

in which:

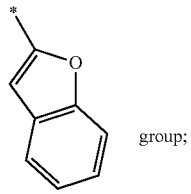 [SMILES: *c1cc2ccccc2o1]

represents a: group;

wherein * indicates the point of attachment of said group with the rest of the molecule; and R1 represents a linear $C_1$-$C_6$-alkyl-, a branched $C_3$-$C_6$-alkyl-, or a $C_3$-$C_6$-cycloalkyl group which is optionally substituted, one or more times, independently from each other, with a substituent selected from:

a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R" group;

R2 represents a hydrogen atom;

R3 represents a substituent selected from:

a halogen atom, a —CN, $C_1$-$C_6$-alkyl-, $C_1$-$C_6$-haloalkyl-, $C_2$-$C_6$-alkenyl-, $C_2$-$C_6$-alkynyl-, —C(=O)R', —C(=O)NH$_2$, —C(=O)N(H)R', —C(=O)N(R')R", —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group;

R4 represents a substituent selected from:

a hydrogen atom, a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl- optionally substituted one or more times, independently from each other, with an R substituent; heteroaryl- optionally substituted one or more times, independently from each other, with an R substituent; —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group;

R represents a substituent selected from:

a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl-, heteroaryl-, —C(=O)R', —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group;

R' and R" represent, independently from each other, a substituent selected from:

a $C_1$-$C_6$-alkyl-, $C_3$-$C_{10}$-cycloalkyl-, $C_1$-$C_6$-haloalkyl group;

R5 represents:

either:

a substituent selected from a $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, $C_3$-$C_{10}$-cycloalkyl-$C_1$-$C_6$-alkyl-, aryl-, —C(=O)NH$_2$, —C(=O)N(H)R', —C(=O)N(R')R", —S(=O)R', —S(=O)$_2$R' group;

or:

together, with the nitrogen atom to which it is bound, and with a carbon atom of R1, form a 3- to 7-membered cyclic secondary amine group, which is optionally substituted with a substituent selected from:

a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R" group;

n represents an integer of 0, 1, 2, 3, 4 or 5;

or a stereoisomer, a tautomer, an N-oxide, a hydrate, a solvate, or a salt thereof, or a mixture of same.

The terms as mentioned in the present text have preferably the following meanings:

The term "halogen atom", "halo-" or "Hal-" is to be understood as meaning a fluorine, chlorine, bromine or iodine atom, preferably a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, in which the term "$C_1$-$C_6$-alkyl" is defined supra, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-inyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl").

The term "$C_4$-$C_{10}$-cycloalkenyl" is to be understood as preferably meaning a monovalent, mono-, or bicyclic hydrocarbon ring which contains 4, 5, 6, 7, 8, 9 or 10 carbon atoms and one, two, three or four double bonds, in conjugation or not, as the size of said cycloalkenyl ring allows. Said $C_4$-$C_{10}$-cycloalkenyl group is for example, a monocyclic hydrocarbon ring, e.g. a cyclobutenyl, cyclopentenyl, or cyclohexenyl or a bicyclic hydrocarbon, e.g.:

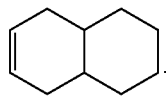

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl-group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused.

Said heterocyclyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "4- to 10-membered heterocycloalkenyl", is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl-group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group, or, it may be benzo fused.

The term "3- to 7-membered cyclic secondary amine group", is to be understood as meaning a group selected from:

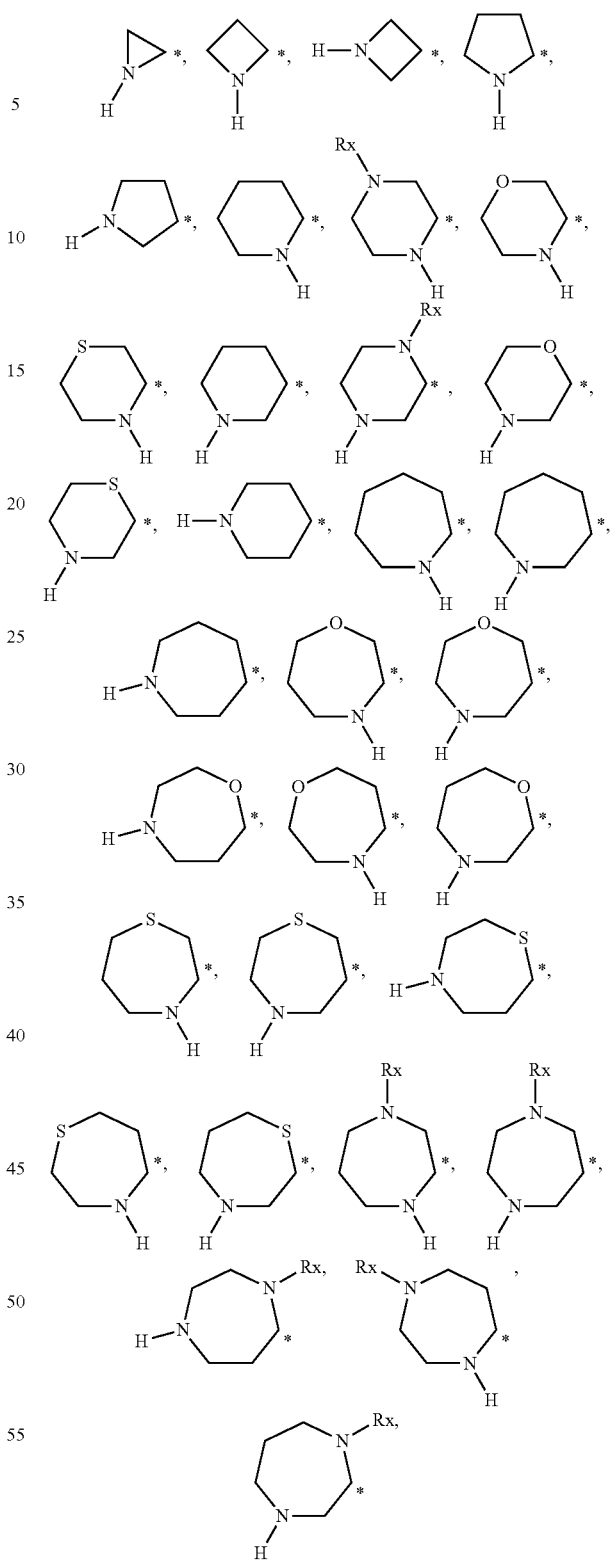

wherein:

Rx represents a hydrogen atom, a $C_1$-$C_6$-alkyl- or halo-$C_1$-$C_6$-alkyl-group; and

* indicates the point of attachment of said group with the rest of the molecule.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

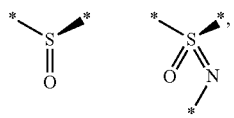

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

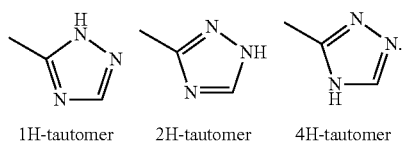

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt.

Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In accordance with a second embodiment of the first aspect, the present invention covers compounds of general formula (I), supra, in which:

represents a:

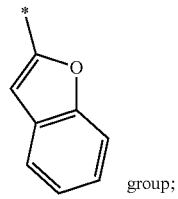

group;

wherein * indicates the point of attachment of said group with the rest of the molecule; and R1 represents a linear $C_1$-$C_6$-alkyl-, a branched $C_3$-$C_6$-alkyl-, or a $C_3$-$C_6$-cycloalkyl group which is optionally substituted, one or more times, independently from each other, with a substituent selected from:

a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R" group;

R2 represents a hydrogen atom;

R3 represents a substituent selected from:

a halogen atom, a —CN, $C_1$-$C_6$-alkyl-, $C_1$-$C_6$-haloalkyl-, —OH, $C_1$-$C_6$-alkoxy-, $C_1$-$C_6$-haloalkoxy-group;

R4 represents a substituent selected from:

a hydrogen atom, a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl- optionally substituted one or more times, independently from each other, with an R substituent; heteroaryl- optionally substituted one or more times, independently from each other, with an R substituent; —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group;

R represents a substituent selected from:

a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl-, heteroaryl-, —C(=O)R', —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')

R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, C$_1$-C$_6$-alkoxy-, C$_1$-C$_6$-haloalkoxy-, —OC(=O)R', —OC(=O)NH$_2$, —OC(=O)NHR', —OC(=O)N(R')R", —SH, C$_1$-C$_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R"group;

R' and R" represent, independently from each other, a substituent selected from:

a C$_1$-C$_6$-alkyl-, C$_3$-C$_{10}$-cycloalkyl-, C$_1$-C$_6$-haloalkyl group;

R5 represents:

either:
a substituent selected from a C$_1$-C$_6$-alkyl-, C$_1$-C$_6$-haloalkyl-, C$_2$-C$_6$-alkenyl-, C$_2$-C$_6$-alkynyl-, C$_3$-C$_{10}$-cycloalkyl-, C$_3$-C$_{10}$-cycloalkyl-C$_1$-C$_6$-alkyl-, aryl-, —C(=O)NH$_2$, —C(=O)N(H)R', —C(=O)N(R')R", —S(=O)R', —S(=O)$_2$R' group;

or:
together, with the nitrogen atom to which it is bound and with a carbon atom of R1, form a 3- to 7-membered cyclic secondary amine group, which is optionally substituted with a substituent selected from:
a halogen atom, a —CN, C$_1$-C$_6$-alkyl-, C$_1$-C$_6$-haloalkyl-, C$_2$-C$_6$-alkenyl-, C$_2$-C$_6$-alkynyl-, C$_3$-C$_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', N(H)S(=O)$_2$R', —N(R')S(=O)$_2$R', —N=S(=O)(R')R", —OH, C$_1$-C$_6$-alkoxy-, C$_1$-C$_6$-haloalkoxy-, —OC(=O)R', —OC(=O)NH$_2$, —OC(=O)NHR', —OC(=O)N(R')R", —SH, C$_1$-C$_6$-alkyl-S—, —S(=O)R', —S(=O)$_2$R', —S(=O)$_2$NH$_2$, —S(=O)$_2$NHR', —S(=O)$_2$N(R')R" group;

n represents an integer of 0, 1, 2, 3, 4 or 5;

or a stereoisomer, a tautomer, an N-oxide, a hydrate, a solvate, or a salt thereof, or a mixture of same.

In accordance with a third embodiment of the first aspect, the present invention covers compounds of general formula (I), supra, in which:

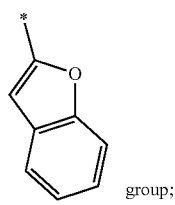

represents a:

group;

wherein * indicates the point of attachment of said group with the rest of the molecule; and R1 represents a linear C$_1$-C$_6$-alkyl-, a branched C$_3$-C$_6$-alkyl-, or a C$_3$-C$_6$-cycloalkyl group which is optionally substituted, one or more times, independently from each other, with a substituent selected from:

a halogen atom, a —CN, C$_1$-C$_6$-alkyl-, C$_1$-C$_6$-haloalkyl-, C$_2$-C$_6$-alkenyl-, C$_2$-C$_6$-alkynyl-, C$_3$-C$_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, C$_1$-C$_6$-alkoxy-, C$_1$-C$_6$-haloalkoxy-, —OC(=O)R', —OC(=O)NH$_2$, —OC(=O)NHR', —OC(=O)N(R')R", —SH, C$_1$-C$_6$-alkyl-S—, —S(=O)R', —S(=O)$_2$R', —S(=O)$_2$NH$_2$, —S(=O)$_2$NHR', —S(=O)$_2$N(R')R" group;

R2 represents a hydrogen atom;

R3 represents a substituent selected from:

a halogen atom, a —CN, C$_1$-C$_6$-alkyl-, C$_1$-C$_6$-haloalkyl-, —OH, C$_1$-C$_6$-alkoxy-, C$_1$-C$_6$-haloalkoxy-group;

R4 represents a substituent selected from:

a hydrogen atom, a halogen atom, a —CN, C$_1$-C$_6$-alkyl-, C$_1$-C$_6$-haloalkyl, C$_3$-C$_{10}$-cycloalkyl-, aryl-, heteroaryl- group;

R' and R" represent, independently from each other, a substituent selected from:

a C$_1$-C$_6$-alkyl-, C$_3$-C$_{10}$-cycloalkyl-, C$_1$-C$_6$-haloalkyl group;

R5 represents:

either:
a substituent selected from a C$_1$-C$_6$-alkyl-, C$_1$-C$_6$-haloalkyl-, C$_2$-C$_6$-alkenyl-, C$_2$-C$_6$-alkynyl-, C$_3$-C$_{10}$-cycloalkyl-, C$_3$-C$_{10}$-cycloalkyl-C$_1$-C$_6$-alkyl-, aryl-, —C(=O)NH$_2$, —C(=O)N(H)R', —C(=O)N(R')R", —S(=O)R', —S(=O)$_2$R' group;

or:
together, with the nitrogen atom to which it is bound and with a carbon atom of R1, form a 3- to 7-membered cyclic secondary amine group;

n represents an integer of 0 or 1;

or a stereoisomer, a tautomer, an N-oxide, a hydrate, a solvate, or a salt thereof, or a mixture of same.

In accordance with a fourth embodiment of the first aspect, the present invention covers compounds of general formula (I), supra, in which:

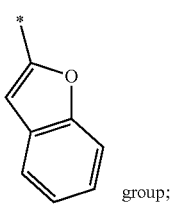

represents a:

group;

wherein * indicates the point of attachment of said group with the rest of the molecule; and R1 represents a linear C$_1$-C$_5$-alkyl-, a branched C$_3$-C$_5$-alkyl-, or a C$_4$-C$_6$-cycloalkyl group which is optionally substituted, one or more times, independently from each other, with a substituent selected from:

a $C_1$-$C_6$-alkyl- or an aryl-group;
R2 represents a hydrogen atom;
R3 represents a substituent selected from:
a halogen atom, a —CN, $C_1$-$C_6$-alkyl-, $C_1$-$C_6$-haloalkyl-, —OH, $C_1$-$C_6$-alkoxy-, $C_1$-$C_6$-haloalkoxy-group;
R4 represents a substituent selected from:
a hydrogen atom, a halogen atom, a —CN, $C_1$-$C_6$-alkyl-, $C_1$-$C_6$-haloalkyl, $C_3$-$C_{10}$-cycloalkyl-, aryl-, heteroaryl-group;
R' and R" represent, independently from each other, a substituent selected from:
a $C_1$-$C_6$-alkyl-, $C_3$-$C_{10}$-cycloalkyl-, $C_1$-$C_6$-haloalkyl group;
R5 represents:
either:
   a substituent selected from a $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, $C_3$-$C_{10}$-cycloalkyl-$C_1$-$C_6$-alkyl-, aryl-, —C(=O)NH$_2$, —C(=O)N(H)R', —C(=O)N(R')R", —S(=O)R', —S(=O)$_2$R' group;
or:
   together, with the nitrogen atom to which it is bound and with a carbon atom of R1, form a 3- to 7-membered cyclic secondary amine group;
n represents an integer of 0 or 1;
or a stereoisomer, a tautomer, an N-oxide, a hydrate, a solvate, or a salt thereof, or a mixture of same.

In accordance with a fifth embodiment of the first aspect, the present invention covers compounds of general formula (I), supra, in which:

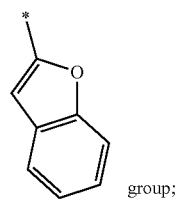

represents a:

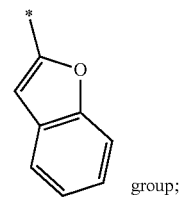

wherein * indicates the point of attachment of said group with the rest of the molecule; and
R1 represents a linear $C_1$-$C_5$-alkyl-group which is optionally substituted, once with a substituent which is:
an aryl-group;
R2 represents a hydrogen atom;
R3 represents a substituent selected from:
a halogen atom, a $C_1$-$C_6$-alkoxy-group; R4 represents a hydrogen atom;
R5 represents:
either:
   a substituent selected from a $C_1$-$C_6$-alkyl-, $C_3$-$C_{10}$-cycloalkyl-, $C_3$-$C_{10}$-cycloalkyl-$C_1$-$C_6$-alkyl-group;
or:
   together, with the nitrogen atom to which it is bound and with a carbon atom of R1, form a 3- to 7-membered cyclic secondary amine group;
n represents an integer of 0 or 1;
or a stereoisomer, a tautomer, an N-oxide, a hydrate, a solvate, or a salt thereof, or a mixture of same.

In a further embodiment of the above-mentioned aspect, the invention relates to compounds of formula (I), wherein:

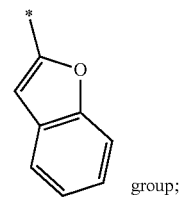

represents a:

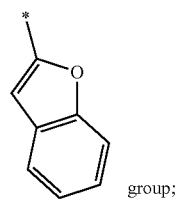 [SMILES: *c1cc2ccccc2o1]

wherein * indicates the point of attachment of said group with the rest of the molecule.

In a further embodiment of the above-mentioned aspect, the invention relates to compounds of formula (I), wherein:
R1 represents a linear $C_1$-$C_6$-alkyl-, a branched $C_3$-$C_6$-alkyl-, or a $C_3$-$C_6$-cycloalkyl group which is optionally substituted, one or more times, independently from each other, with a substituent selected from:
a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R" group.

In a further embodiment of the above-mentioned aspect, the invention relates to compounds of formula (I), wherein:
R2 represents a hydrogen atom.

In a further embodiment of the above-mentioned aspect, the invention relates to compounds of formula (I), wherein:
R3 represents a substituent selected from:
a halogen atom, a —CN, $C_1$-$C_6$-alkyl-, $C_1$-$C_6$-haloalkyl-, $C_2$-$C_6$-alkenyl-, $C_2$-$C_6$-alkynyl-, —C(=O)R', —C(=O)NH$_2$, —C(=O)N(H)R', —C(=O)N(R')R", —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group.

In a further embodiment of the above-mentioned aspect, the invention relates to compounds of formula (I), wherein:
R4 represents a substituent selected from:
a hydrogen atom, a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl- optionally substituted one or more times, independently from each other, with an R substituent; heteroaryl- optionally substituted one or more times, independently from each other, with an R substituent; —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, C$_1$-C$_6$-alkoxy-, C$_1$-C$_6$-haloalkoxy-, —OC(=O)R', —OC(=O)NH$_2$, —OC(=O)NHR', —OC(=O)N(R')R", —SH, C$_1$-C$_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group.

In a further embodiment of the above-mentioned aspect, the invention relates to compounds of formula (I), wherein:
R' and R" represent, independently from each other, a substituent selected from:
a C$_1$-C$_6$-alkyl-, C$_3$-C$_{10}$-cycloalkyl-, C$_1$-C$_6$-haloalkyl group.

In a further embodiment of the above-mentioned aspect, the invention relates to compounds of formula (I), wherein:
R5 represents:
a substituent selected from a C$_1$-C$_6$-alkyl-, C$_1$-C$_6$-haloalkyl-, C$_2$-C$_6$-alkenyl-, C$_2$-C$_6$-alkynyl-, C$_3$-C$_{10}$-cycloalkyl-, C$_3$-C$_{10}$-cycloalkyl-C$_1$-C$_6$-alkyl-, aryl-, —C(=O)NH$_2$, —C(=O)N(H)R', —C(=O)N(R')R", —S(=O)R', —S(=O)$_2$R' group.

In a further embodiment of the above-mentioned aspect, the invention relates to compounds of formula (I), wherein:
R5 represents:
together, with the nitrogen atom to which it is bound, and with a carbon atom of R1, form a 3- to 7-membered cyclic secondary amine group, which is optionally substituted with a substituent selected from:
a halogen atom, a —CN, C$_1$-C$_6$-alkyl-, C$_1$-C$_6$-haloalkyl-, C$_2$-C$_6$-alkenyl-, C$_2$-C$_6$-alkynyl-, C$_3$-C$_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', N(H)S(=O)$_2$R', —N(R')S(=O)$_2$R', —N=S(=O)(R')R", —OH, C$_1$-C$_6$-alkoxy-, C$_1$-C$_6$-haloalkoxy-, —OC(=O)R', —OC(=O)NH$_2$, —OC(=O)NHR', —OC(=O)N(R')R", —SH, C$_1$-C$_6$-alkyl-S—, —S(=O)R', —S(=O)$_2$R', —S(=O)$_2$NH$_2$, —S(=O)$_2$NHR', —S(=O)$_2$N(R')R" group.

In a further embodiment of the above-mentioned aspect, the invention relates to compounds of formula (I), wherein:
n represents an integer of 0, 1, 2, 3, 4 or 5.

In a further embodiment of the above-mentioned aspect, the invention relates to compounds of formula (I), wherein:
R3 represents a substituent selected from:
a halogen atom, a —CN, C$_1$-C$_6$-alkyl-, C$_1$-C$_6$-haloalkyl-, —OH, C$_1$-C$_6$-alkoxy-, C$_1$-C$_6$-haloalkoxy-group;

In a further embodiment of the above-mentioned aspect, the invention relates to compounds of formula (I), wherein:
R4 represents a substituent selected from:
a hydrogen atom, a halogen atom, a —CN, C$_1$-C$_6$-alkyl-, C$_1$-C$_6$-haloalkyl, C$_3$-C$_{10}$-cycloalkyl-, aryl-, heteroaryl-group.

In a further embodiment of the above-mentioned aspect, the invention relates to compounds of formula (I), wherein:
R5 represents:
together, with the nitrogen atom to which it is bound and with a carbon atom of R1, form a 3- to 7-membered cyclic secondary amine group.

In a further embodiment of the above-mentioned aspect, the invention relates to compounds of formula (I), wherein:
n represents an integer of 0 or 1.

In a further embodiment of the above-mentioned aspect, the invention relates to compounds of formula (I), wherein:
R1 represents a linear C$_1$-C$_5$-alkyl-, a branched C$_3$-C$_5$-alkyl-, or a C$_4$-C$_6$-cycloalkyl group which is optionally substituted, one or more times, independently from each other, with a substituent selected from:
a C$_1$-C$_6$-alkyl- or an aryl-group.

In a further embodiment of the above-mentioned aspect, the invention relates to compounds of formula (I), wherein:
R1 represents a linear C$_1$-C$_5$-alkyl-group which is optionally substituted, once with a substituent which is:
an aryl-group.

In a further embodiment of the above-mentioned aspect, the invention relates to compounds of formula (I), wherein:
R3 represents a substituent selected from:
a halogen atom, a C$_1$-C$_6$-alkoxy-group.

In a further embodiment of the above-mentioned aspect, the invention relates to compounds of formula (I), wherein:
R4 represents a hydrogen atom.

In a further embodiment of the above-mentioned aspect, the invention relates to compounds of formula (I), wherein:
R' and R" represent, independently from each other, a substituent selected from:
a C$_1$-C$_6$-alkyl-, C$_3$-C$_{10}$-cycloalkyl-group.

In a further embodiment of the above-mentioned aspect, the invention relates to compounds of formula (I), wherein:
R5 represents:
a substituent selected from a C$_1$-C$_6$-alkyl-, C$_3$-C$_{10}$-cycloalkyl-, C$_3$-C$_{10}$-cycloalkyl-C$_1$-C$_6$-alkyl-group.

In a further embodiment of the above-mentioned aspect, the invention relates to compounds of formula (I), wherein:
n represents an integer of 0.

In a further embodiment of the above-mentioned aspect, the invention relates to compounds of formula (I), wherein:
n represents an integer of 1.

In a further embodiment of the above-mentioned aspect, the invention relates to compounds of formula (I), according to any of the above-mentioned embodiments, in the form of or a stereoisomer, a tautomer, an N-oxide, a hydrate, a solvate, or a salt thereof, or a mixture of same.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In accordance with a further aspect, the present invention covers intermediate compounds which are useful in the preparation of compounds of the present invention of general formula (I), particularly in the method described herein. In particular, the present invention covers compounds of general formula (V):

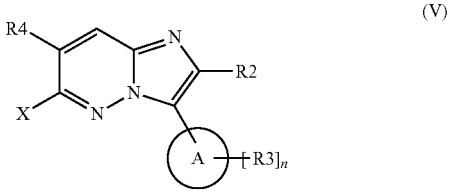

(V)

in which A, R2, R3, R4 and n are as defined for the compound of general formula (I) supra, and X represents a leaving group, such as a halogen atom, for example a chlorine, bromine or iodine atom, or a perfluoroalkylsulfonate group for example, such as a trifluoromethylsulfonate group or a nonafluorobutylsulfonate group, for example.

In accordance with yet another aspect, the present invention covers the use of the intermediate compounds of general formula (V):

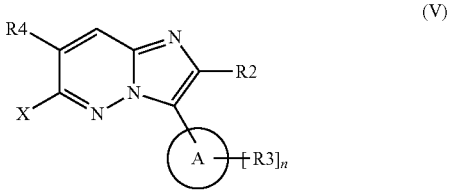

(V)

in which A, R2, R3, R4 and n are as defined for the compound of general formula (I) supra, and X represents a leaving group, such as a halogen atom, for example a chlorine, bromine or iodine atom, or a perfluoroalkylsulfonate group for example, such as a trifluoromethylsulfonate group for example, for the preparation of a compound of general formula (I) as defined supra.

EXPERIMENTAL SECTION

The following table lists the abbreviations used in this paragraph, and in the examples section.

| Abbreviation | Meaning |
|---|---|
| DMF | dimethyl formamide |
| DMSO | dimethyl sulfoxide |
| THF | tetrahydrofurane |
| NMR | nuclear magnetic resonance |
| MS | mass spectroscopy |
| $R_t$ | retention time |

-continued

| Abbreviation | Meaning |
|---|---|
| HPLC, LC | high performance liquid chromatography |
| H | hour |
| min | minute |

Syntheses of Compounds (Overview)

The compounds of the present invention can be prepared as described in the following section. Scheme 1 and the procedures described below illustrate general synthetic routes to the compounds of general formula (I) of the invention and are not intended to be limiting. It is clear to the person skilled in the art that the order of transformations as exemplified in Scheme 1 can be modified in various ways. The order of transformations exemplified in the Scheme 1 is therefore not intended to be limiting. In addition, interconversion of any of the substituents, R1, R2, R3, R4, R5 and A, can be achieved before and/or after the exemplified transformations. These modifications can be such as the introduction of protecting groups, cleavage of protecting groups, exchange, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, $3^{rd}$ edition, Wiley 1999). Specific examples are described in the subsequent paragraphs. Further, it is possible that two or more successive steps may be performed without work-up being performed between said steps, e.g. a "one-pot" reaction, as is well-known to the person skilled in the art.

Scheme 1:

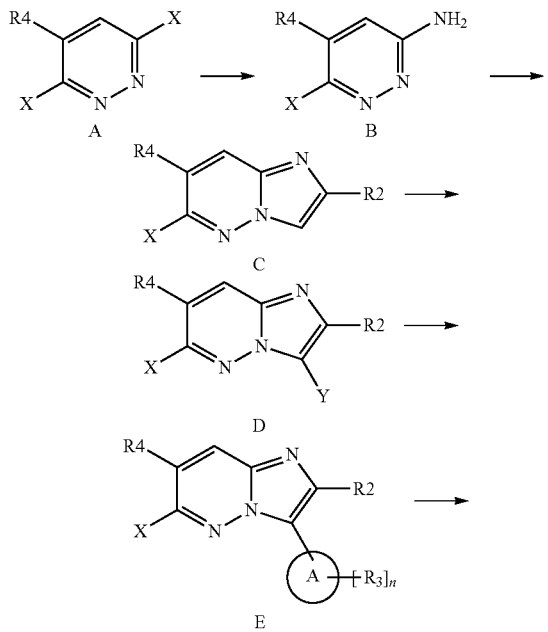

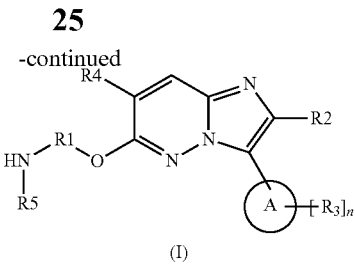

(I)

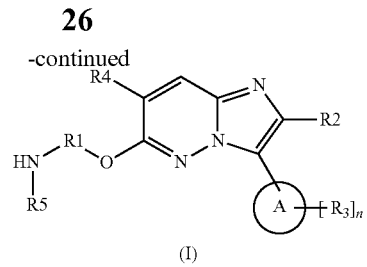

(I)

in which A, R1 R2, R3, R4, R5 and n are as defined supra, and X and Y represent a leaving group, such as a halogen atom, for example a chlorine, bromine or iodine atom, or a perfluoroalkylsulfonate group for example, such as a trifluoromethylsulfonate group, a nonafluorobutylsulfonate group, for example.

In the first step, a compound of formula A, i.e. a dichloropyridazine bearing suitable X substituents, can be reacted with ammonia at elevated temperature and pressure to give a compound of general formula B. [in analogy to WO200733080, which is hereby incorporated herein in its entirety as reference]

In the second step, a compound of general formula B reacts, for example, with chloroacetaldehyde or bromoacetaldehyde diacetal to give the bicyclic ring system C [in analogy to DE102006029447, which is hereby incorporated herein in its entirety as reference].

Activation of position 3 of the bicyclic system to give compounds of general formula D can be accomplished, for example, by bromination or iodination of compounds of general formula C using N-bromo-succinimide or N-iodo-succinimide, respectively.

In the fourth step, introduction of residue A-[R3]$_n$ can be achieved using suitably catalyzed cross-coupling reactions employing, for example, boronic acids or stannanes, which results in compounds of general formula E.

Compounds of general formula E serve as central intermediates for the introduction of various side chains containing an alcohol function, which results in imidazopyridazinyl-ethers of general formula (I). Introduction of the side chains can be achieved, for example, by employing bases such as sodium hydride. Depending on the nature of the side chain it may be necessary to run these reactions at elevated temperatures. It may also be necessary to introduce side chains bearing suitable protecting groups on functional groups which may disturb the desired reaction.

The fourth and the fifth step of the described sequence may also be interconverted as illustrated in Scheme 2.

Scheme 2:

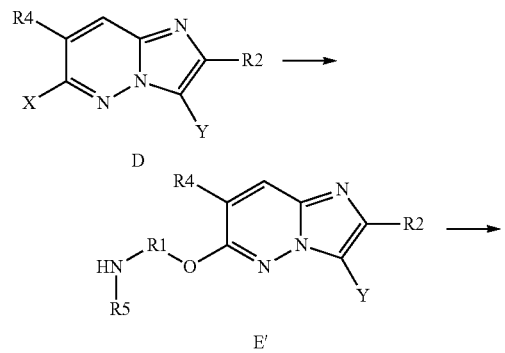

In accordance with an embodiment, the present invention also relates to a method of preparing a compound of general formula (I) as defined supra, said method comprising the step of allowing an intermediate compound of general formula (V):

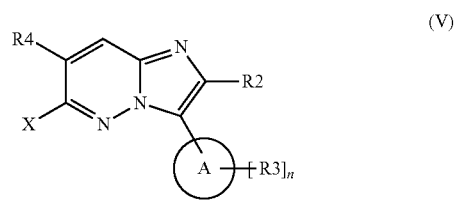

in which A, R2, R3, R4 and n are as defined for the compound of general formula (I) supra, and X represents a leaving group, such as a halogen atom, for example a chlorine, bromine or iodine atom, or a perfluoroalkylsulfonate group for example, such as a trifluoromethylsulfonate group, a nonafluorobutylsulfonate group, for example, to react with a compound of general formula (III):

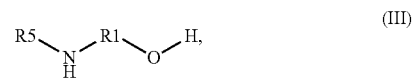

in which R1 and R5 are as defined for the compound of general formula (I), supra, thereby giving a compound of general formula (I):

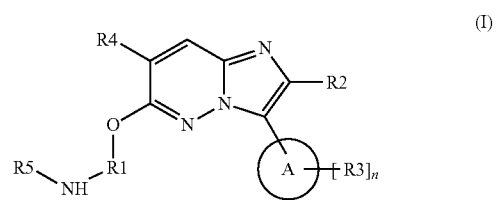

in which A, R1, R2, R3, R4, R5 and n are as defined supra.

General Part

Chemical names were generated using ACD/Name Batch Version 12.01.

HPLC Methods:

Method 1:

Instrument: Waters Acquity UPLCMS ZQ4000; Column: Acquity UPLC BEH C18 1.7 μm, 50×2.1 mm; eluent A: water+0.05 vol % formic acid, Eluent B: acetonitrile+0.05 vol % formic acid gradient: 0-1.6 min 1-99% B, 1.6-2.0 min 99% B; flow 0.8 mL/min; temperature: 60° C.; injection: 2 μL; DAD scan: 210-400 nm; ELSD Method 2:

Instrument: Waters Acquity UPLCMS SQD 3001; Column: Acquity UPLC BEH C18 1.7 μm, 50×2.1 mm; eluent A: water+0.1 vol % formic acid (95%), eluent B: acetonitrile, gradient: 0-1.6 min 1-99% B, 1.6-2.0 min 99% B; flow 0.8 mL/min; temperature: 60° C.; injection: 2 μL; DAD scan: 210-400 nm; ELSD Method 3:

Instrument: Waters Acquity UPLCMS SQD; Column: Acquity UPLC BEH C18 1.7 μm, 50×2.1 mm; eluent A: water+0.05 vol % formic acid (95%), eluent B: acetonitrile+ 0.05 vol % formic acid (95%), gradient: 0-1.6 min 1-99% B, 1.6-2.0 min 99% B; flow 0.8 mL/min; temperature: 60° C.; injection: 2 μL; DAD scan: 210-400 nm; ELSD Method 4:

Instrument: Waters Acquity UPLC-MS SQD; Column: Acquity UPLC BEH C18 1.7 50×2.1 mm; eluent A: water+ 0.1 vol % formic acid (99%), eluent B: acetonitrile; gradient: 0-1.6 min 1-99% B, 1.6-2.0 min 99% B; flow 0.8 mL/min; temperature: 60° C.; injection: 2 μl; DAD scan: 210-400 nm; ELSD

INTERMEDIATES

Intermediate 1

3-Bromo-6-chloro-imidazo[1,2-b]pyridazine

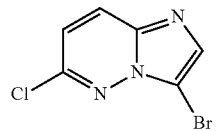 [SMILES: Clc1ccc2ncc(Br)n2n1]

3-Bromo-6-chloro-imidazo[1,2-b]pyridazine was synthesised as described for example in WO 2007/147646 or DE 10 2006 029447, e.g. as follows:

Step 1: Preparation of 6-Chloroimidazo[1,2-b]pyridazine

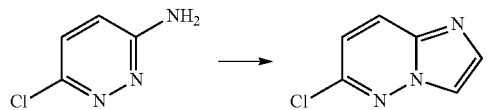 [SMILES: Nc1ccc(Cl)nn1 ; Clc1ccc2nccn2n1]

5.0 g (38.6 mmol) of 3-amino-6-chloropyridazine were heated together with 4.7 mL (40 mmol) of chloracetaldehyde (55% strength in water) in 15 mL of n-butanol at 120° C. for a period of 5 days. After the reaction was complete, the reaction mixture was added to saturated sodium bicarbonate solution and extracted three times with ethyl acetate. The combined organic phases were then washed with sat. sodium chloride solution and dried over sodium sulfate, and the solvent was removed in vacuo. In the final purification by chromatography on silica gel, 4.17 g (70%) of the desired product were isolated in the form of an amorphous white solid.

$^1$H-NMR (CHLOROFORM-d): δ [ppm]=7.06 (1H); 7.79 (1H); 7.92 (1H); 7.96 (1H).

Step 2: Preparation of 3-Bromo-6-chloroimidazo[1,2-b] pyridazine

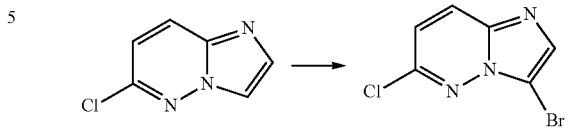

478 mg (3.11 mmol) of 6-chloroimidazo[1,2-b]pyridazine were introduced into 10 mL of chloroform under argon and, while cooling in ice, 664 mg (3.73 mmol) of N-bromosuccuinimide were added. After the addition was complete, the reaction mixture was stirred at room temperature overnight. The reaction mixture was then mixed with water and ethyl acetate and, after addition of saturated sodium bicarbonate solution, the phases were separated. The aqueous phase was extracted three more times with ethyl acetate. The combined organic phases were then washed with sat. sodium chloride solution and dried over sodium sulfate. In the final removal of the solvent in vacuo, the desired product was isolated in quantitative yield in the form of an amorphous white solid which was employed without further chromatographic purification in subsequent reactions.

$^1$H-NMR (CHLOROFORM-d): δ [ppm]=7.12 (1H); 7.79 (1H); 7.90 (1H).

Intermediate 2

3-(1-Benzofur-2-yl)-6-chloroimidazo[1,2-b] pyridazine

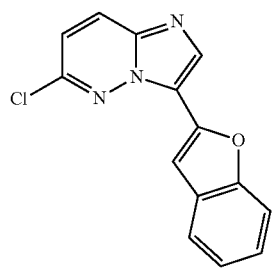 [SMILES: Clc1ccc2ncc(-c3cc4ccccc4o3)n2n1]

13.9 g (59.8 mmol) 3-bromo-6-chloro-imidazo[1,2-b] pyridazine were suspended in 508 mL 1,4-dioxane. 10.1 g (62.8 mmol) 2-benzofuranylboronic acid, 2.76 g (2.29 mmol) tetrakis(triphenylphosphino)palladium-(0) and 90 mL (180 mmol) of a 2M aqueous sodium carbonate solution were added. The obtained mixture was heated to 100° C. for 24 h.

400 mL of a saturated aqueous ammonium chloride solution were added. The obtained mixture was extracted with ethyl acetate. The combined organic layers were washed with brine and dried over magnesium sulfate. After evaporation of the solvent, the obtained solid material was digested in 40 mL of a mixture of dichloromethane and methanol (8:2), filtered off and dried in vacuo to yield 5.42 g (44%) of the title compound as solid material.

$^1$H-NMR (300 MHz, DMSO-d$_6$): δ [ppm]=7.23-7.40 (2H), 7.51 (1H), 7.59-7.67 (2H), 7.77 (1H), 8.33-8.40 (2H).

LCMS (Method 1): R$_t$=1.35 min; MS (ESIpos) m/z=270 [M+H]$^+$.

Intermediate 3

6-Chloro-3-(4-methoxy-1-benzofuran-2-yl)imidazo[1,2-b]pyridazine

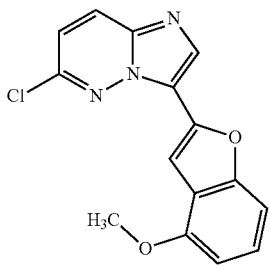 [SMILES: COc1cccc2oc(-c3cnc4ccc(Cl)nn34)cc12]

6-Chloro-3-(4-methoxy-1-benzofuran-2-yl)imidazo[1,2-b]pyridazine was prepared in analogy to 3-(1-benzofur-2-yl)-6-chloroimidazo[1,2-b]pyridazine starting from 1.68 g (7.22 mmol) of 3-bromo-6-chloroimidazo[1,2-b]pyridazine to yield 43% of a solid material.

$^1$H-NMR (300 MHz, DMSO-$d_6$), δ [ppm]=3.96 (3H), 6.85-6.91 (1H), 7.25-7.38 (2H), 7.52-7.59 (2H), 8.37-8.43 (2H)

LCMS (Method 1): $R_t$=1.31 min; MS (ESIpos) m/z=300 [M+H]$^+$.

Intermediate 4

6-Chloro-3-(5-methoxy-1-benzofuran-2-yl)imidazo[1,2-b]pyridazine

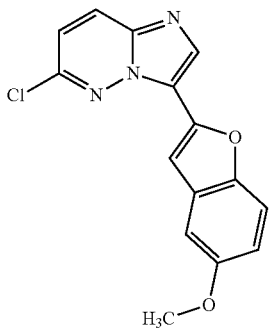 [SMILES: COc1ccc2oc(-c3cnc4ccc(Cl)nn34)cc2c1]

6-Chloro-3-(5-methoxy-1-benzofuran-2-yl)imidazo[1,2-b]pyridazine was prepared in analogy to 3-(1-benzofur-2-yl)-6-chloroimidazo[1,2-b]pyridazine starting from 1.74 g (7.5 mmol) of 3-bromo-6-chloroimidazo[1,2-b]pyridazine to yield 45% of a solid material.

$^1$H-NMR (300 MHz, DMSO-$d_6$), δ [ppm]=3.81 (3H), 6.91-6.99 (1H), 7.33 (1H), 7.50-7.60 (3H), 8.35-8.42 (2H).

LCMS (Method 1): $R_t$=1.29 min; MS (ESIpos) m/z=300 [M+H]$^+$.

Intermediate 5

6-Chloro-3-(5-chloro-1-benzofuran-2-yl)imidazo[1,2-b]pyridazine

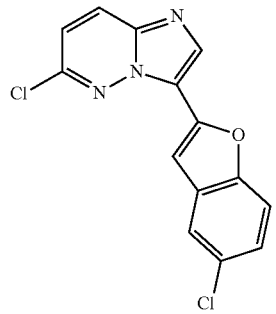 [SMILES: Clc1ccc2oc(-c3cnc4ccc(Cl)nn34)cc2c1]

Step 1: A mixture of 2 g (13 mmol) 7-chloro-1-benzofuran in dry THF (100 mL) was cooled to −78° C. 7.9 ml (19.7 mmol) of a solution of n-butyllithium in hexane was added and the resulting mixture was stirred for 1 h at −78° C. 5.3 mL (19.7 mmol) of tributyltin chloride was added. The reaction was stirred at room temperature over night.

Methanol was carefully added and the solvent evaporated. The obtained residue was purified by flash chromatography to yield 6.2 g of crude product of the corresponding 2-stannylbenzofurane, which was used without further purification in step 2.

Step 2: In an inert atmosphere, 2.34 g (10.1 mmol) of 3-bromo-6-chloro-imidazo[1,2-b]pyridazine, 5.79 g (13.1 mmol) of the crude 2-stannylbenzofurane from step 1, 192 mg (1 mmol) copper (I) iodide and 354 mg (0.5 mmol) bis(triphenylphosphine) palladium(II)chloride in 100 mL of THF is stirred for 19 h at 85° C. in a sealed pressure tube. The solvent was evaporated, the obtained solid was digested in methanol and filtered off to yield 2.73 g of the title compound as solid material which was used as crude product in the subsequent reactions.

LCMS (Method 3): $R_t$=1.00 min; MS (ESIpos) m/z=304 [M+H]$^+$.

Intermediate 6

6-Chloro-3-(5-fluoro-1-benzofuran-2-yl)imidazo[1,2-b]pyridazine

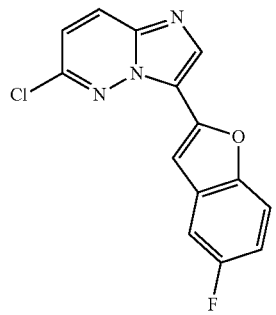 [SMILES: Fc1ccc2oc(-c3cnc4ccc(Cl)nn34)cc2c1]

6-Chloro-3-(5-fluoro-1-benzofuran-2-yl)imidazo[1,2-b]pyridazine was prepared in analogy to 6-chloro-3-(5-chloro-1-benzofuran-2-yl)imidazo[1,2-b]pyridazine starting from 513 mg (2.21 mmol) of 3-bromo-6-chloroimidazo[1,2-b]pyridazine to yield 166 mg of a solid material (approx. 57% pure). This material was used in subsequent steps without further purification LCMS (Method 4): $R_t$=1.37 min; MS (ESIpos) m/z=288 [M+H]+.

Intermediate 7

6-Chloro-3-(4-fluoro-1-benzofuran-2-yl)imidazo[1,2-b]pyridazine

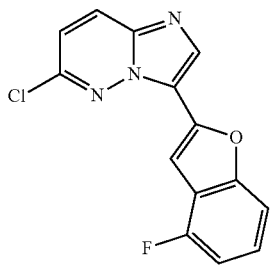 [SMILES: Fc1cccc2oc(-c3cnc4ccc(Cl)nn34)cc12]

6-Chloro-3-(4-fluoro-1-benzofuran-2-yl)imidazo[1,2-b]pyridazine was prepared in analogy to 6-chloro-3-(5-chloro-1-benzofuran-2-yl)imidazo[1,2-b]pyridazine starting from 921 mg (3.96 mmol) of 3-bromo-6-chloroimidazo[1,2-b]pyridazine to yield 929 mg of a solid material which was used as crude product.

1H-NMR (300 MHz, DMSO-$d_6$), δ [ppm]=7.09-7.23 (1H), 7.32-7.45 (1H), 7.55 (3H), 8.41 (2H).

LCMS (Method 3): Rt=1.42 min; MS (ESIpos) m/z=288 [M+H]+.

EXAMPLES

Example 1

3-(1-Benzofuran-2-yl)-6-[2-(morpholin-2-yl)ethoxy]imidazo[1,2-b]pyridazine

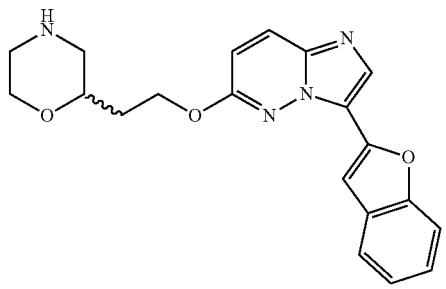 [SMILES: c1ccc2oc(-c3cnc4ccc(OCCC5CNCCO5)nn34)cc2c1]

In an ice bath, 68.1 mg (0.52 mmol) 2-(2-morpholinyl)ethanol were added to 18.3 mg (0.46 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 72 h at 40° C.

The reaction mixture was poured into water, and extracted with ethyl acetate. The organic layer was dried over magnesium sulfate, and concentrated. The residue was purified by HPLC to yield 45 mg (47%) product as solid material.

$^1$H-NMR (400 MHz, DMSO-$d_6$), δ [ppm]=1.86-1.96 (2H), 2.40 (1H), 2.56-2.68 (2H), 2.82 (1H), 3.43 (1H), 3.52-3.60 (1H), 3.73 (1H), 4.53-4.60 (2H), 7.01 (1H), 7.24-7.35 (2H), 7.59-7.65 (2H), 7.67-7.74 (1H), 8.10-8.18 (2H).

LC-MS (Method 3): $R_t$=0.78 min; MS (ESIpos) m/z=365 [M+H]$^+$.

Example 2

3-(4-Methoxy-1-benzofuran-2-yl)-6-[(2R)-morpholin-2-ylmethoxy]imidazo[1,2-b]pyridazine

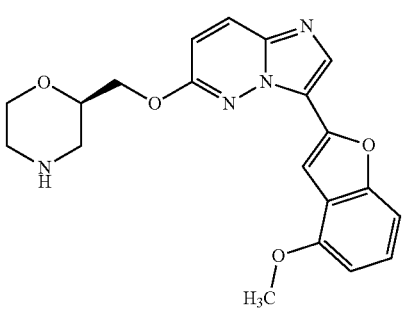 [SMILES: COc1cccc2oc(-c3cnc4ccc(OC[C@H]5CNCCO5)nn34)cc12]

In an ice bath, 191 mg (1.6 mmol) (R)-2-hydroxymethylmorpholine were added to 64 mg (1.6 mmol) sodium hydride (60% in mineral oil) in 24 mL anhydrous tetrahydrofurane. After 15 min of stirring in the ice bath, 120 mg (0.4 mmol) 6-chloro-3-(4-methoxy-1-benzofuran-2-yl)-imidazo[1,2-b]pyridazine were added. The ice bath was removed and the reaction mixture was stirred for 24 h at room temperature.

The reaction mixture was poured into saturated aqueous ammonium chloride solution, and extracted with ethyl acetate. The organic layer was dried over magnesium sulfate, and concentrated. The residue was purified by HPLC to yield 21 mg (14%) product as solid material.

$^1$H-NMR (300 MHz, DMSO-$d_6$), δ [ppm]=2.63-2.73 (3H), 2.95 (1H), 3.48 (1H), 3.77 (1H), 3.92 (4H), 4.41 (2H), 6.83 (1H), 7.04 (1H), 7.19-7.33 (2H), 7.53 (1H), 8.02-8.18 (2H).

LC-MS (Method 3): $R_t$=0.81 min; MS (ESIpos) m/z=381 [M+H]$^+$.

Example 3

3-(1-Benzofuran-2-yl)-6-(morpholin-2-ylmethoxy)imidazo[1,2-b]pyridazine

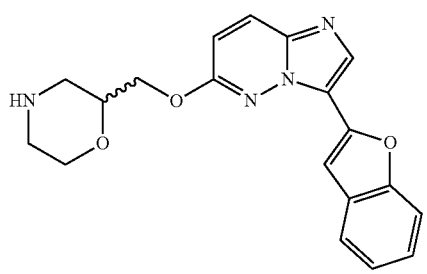 [SMILES: c1ccc2oc(-c3cnc4ccc(OCC5CNCCO5)nn34)cc2c1]

Step 1: In an ice bath, 2.0 g (8.9 mmol) tert.-butyl 2-(hydroxymethyl)morpholine-4-carboxylate were added to 188 mg (7.83 mmol) sodium hydride (60% in mineral oil) in 24 mL anhydrous tetrahydrofurane. After 15 min of stirring in the ice bath, 1.2 g (4.45 mmol) 3-(1-benzofur-2-yl)-6-chloroimidazo[1,2-b]pyridazine were added. The ice bath was removed and the reaction mixture was stirred for 4 days at room temperature.

The reaction mixture was poured into saturated aqueous ammoniumchloride solution, and extracted with ethyl acetate. The combined organic phases were washed with brine, dried over magnesium sulfate, and concentrated. The obtained crude product (3.3 g) was used without further purification in step 2.

Step 2: To 2.2 g of the crude product from step 1 in 36 mL dichloromethane were added 8.9 mL of trifluoroacetic acid. The mixture was stirred for 3 h. Aqueous ammonia was added until the mixture reached basic pH. Brine was added and the mixture extracted with dichloromethane. The organic layer was separated, dried over magnesium sulfate and concentrated. 1.68 g of a solid material were obtained as crude product.

A small sample (75 mg) were purified by HPLC to give 18 mg of the product as solid material.

$^1$H-NMR (300 MHz, DMSO-$d_6$), δ [ppm]=2.64-2.75 (3H), 2.94-3.02 (1H), 3.51 (1H), 3.76-3.92 (1H), 4.45 (2H), 7.06 (1H), 7.23-7.37 (2H), 7.60-7.66 (1H), 7.72 (1H), 8.12-8.19 (2H).

LC-MS (Method 3): $R_t$=0.81 min; MS (ESIpos) m/z=381 [M+H]$^+$.

Example 4

N-(3-{[3-(1-Benzofuran-2-yl)imidazo[1,2-b]pyridazin-6-yl]oxy}propyl)-2,2-dimethylpropan-1-amine

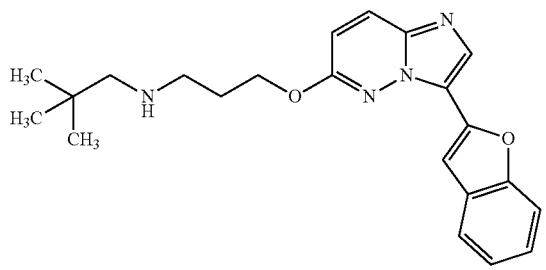 [SMILES: CC(C)(C)CNCCCOc1ccc2ncc(-c3cc4ccccc4o3)n2n1]

In an ice bath, 75 mg (0.52 mmol) (3-[(2,2-dimethylpropyl)amino]propan-1-ol were added to 18 mg (0.45 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 16 h at 40° C.

The reaction mixture was poured into water, and extracted with ethyl acetate. The organic layer was dried over magnesium sulfate, and concentrated. The residue was purified by HPLC to yield 56 mg (57%) product as solid material.

$^1$H-NMR (400 MHz, DMSO-$d_6$), δ [ppm]=0.83 (9H), 1.93-2.02 (2H), 2.26 (2H), 2.72 (2H), 4.56 (2H), 7.00 (1H), 7.24-7.35 (2H), 7.58 (1H), 7.60-7.64 (1H), 7.66-7.70 (1H), 8.13 (2H).

LC-MS (Method 4): $R_t$=0.90 min; MS (ESIpos) m/z=379 [M+H]$^+$.

Example 5

3-(5-Methoxy-1-benzofuran-2-yl)-6-[(2R)-morpholin-2-ylmethoxy]imidazo[1,2-b]pyridazine

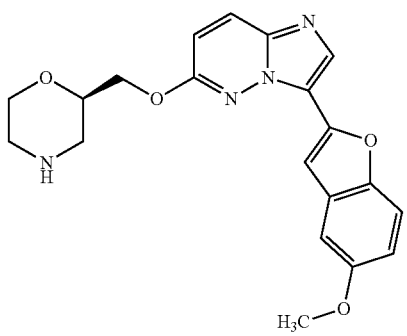 [SMILES: COc1ccc2oc(-c3cnc4ccc(OC[C@H]5CNCCO5)nn34)cc2c1]

In an ice bath, 191 mg (1.6 mmol) (R)-2-hydroxymethylmorpholine were added to 64 mg (1.6 mmol) sodium hydride (60% in mineral oil) in 3 mL anhydrous tetrahydrofurane. After 15 min of stirring in the ice bath, 120 mg (0.40 mmol) 6-chloro-3-(5-methoxy-1-benzofuran-2-yl)imidazo[1,2-b]pyridazine were added. The ice bath was removed and the reaction mixture was stirred for 24 h at room temperature.

The reaction mixture was poured into saturated aqueous ammonium chloride solution, and extracted with ethyl acetate. The organic layer was dried over magnesium sulfate, and concentrated. The residue was purified by HPLC to yield 20 mg (13%) product as solid material.

$^1$H-NMR (300 MHz, DMSO-$d_6$), δ [ppm]=2.66-2.71 (3H), 2.87-2.96 (1H), 3.41-3.56 (1H), 3.79 (5H), 4.42 (2H), 6.90 (1H), 7.04 (1H), 7.24 (1H), 7.48-7.58 (2H), 8.06-8.19 (2H).

LC-MS (Method 3): $R_t$=0.83 min; MS (ESIpos) m/z=381 [M+H]$^+$.

Example 6

2-{[3-(1-Benzofuran-2-yl)imidazo[1,2-b]pyridazin-6-yl]oxy}-N-(cyclopropylmethyl)ethanamine

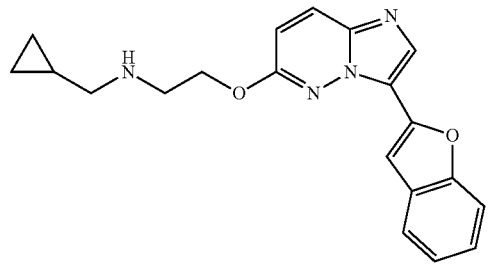 [SMILES: c1ccc2oc(-c3cnc4ccc(OCCNCC5CC5)nn34)cc2c1]

In an ice bath, 87 mg (0.74 mmol) 2-[(cyclopropylmethyl)amino]ethan-1-ol were added to 26 mg (0.65 mmol) sodium hydride (60% in mineral oil) in 5 mL anhydrous tetrahydrofurane. After 15 min of stirring in the ice bath, 100 mg (0.37 mmol) 3-(1-benzofur-2-yl)-6-chloroimidazo[1,2-b]

pyridazine were added. The ice bath was removed and the reaction mixture was stirred for 16 h at 40° C.

The reaction mixture was poured into saturated aqueous ammonium chloride, and extracted with ethyl acetate. The organic layer was dried over magnesium sulfate, and concentrated. The residue was purified by HPLC to yield 56 mg (43%) product as solid material.

¹H-NMR (300 MHz, DMSO-d₆), δ [ppm]=0.08-0.17 (2H), 0.34-0.45 (2H), 0.85-0.98 (1H), 2.54 (2H), 3.11 (2H), 4.58 (2H), 7.03 (1H), 7.23-7.37 (2H), 7.59-7.66 (2H), 7.71 (1H), 8.12-8.23 (2H).

LC-MS (Method 4): $R_t$=0.82 min; MS (ESIpos) m/z=349 [M+H]⁺.

Example 7

3-(1-Benzofuran-2-yl)-6-[(2R)-morpholin-2-ylmethoxy]imidazo[1,2-b]pyridazine

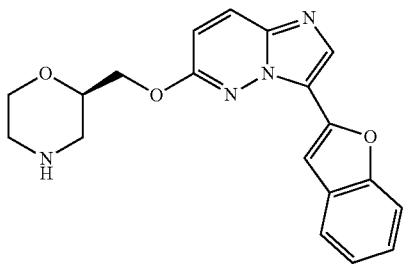 [SMILES: c1ccc2oc(-c3cnc4ccc(OC[C@H]5CNCCO5)nn34)cc2c1]

In an ice bath, 355 mg (2.97 mmol) (R)-2-hydroxymethylmorpholine were added to 119 mg (2.97 mmol) sodium hydride (60% in mineral oil) in 6 mL anhydrous tetrahydrofurane. After 15 min of stirring in the ice bath, 200 mg (0.74 mmol) 3-(1-benzofur-2-yl)-6-chloroimidazo[1,2-b]pyridazine were added. The ice bath was removed and the reaction mixture was stirred for 24 h at room temperature.

The reaction mixture was poured into saturated aqueous ammonium chloride, and extracted with ethyl acetate. The organic layer was dried over magnesium sulfate, and concentrated. The residue was purified by HPLC to yield 67 mg (25%) product as solid material.

¹H-NMR (300 MHz, DMSO-d₆), δ [ppm]=2.62-2.73 (3H), 2.92-3.02 (1H), 3.43-3.57 (1H), 3.72-3.93 (2H), 4.44 (2H), 7.05 (1H), 7.21-7.40 (2H), 7.59-7.66 (2H), 7.70-7.75 (1H), 8.12-8.20 (2H).

LC-MS (Method 3): $R_t$=0.78 min; MS (ESIpos) m/z=351 [M+H]⁺.

Example 8

3-(1-Benzofuran-2-yl)-6-{2-[(3R)-morpholin-3-yl]ethoxy}imidazo[1,2-b]pyridazine

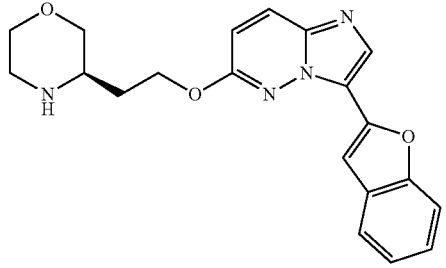 [SMILES: c1ccc2oc(-c3cnc4ccc(OCC[C@@H]5COCCN5)nn34)cc2c1]

In an ice bath, 68 mg (0.52 mmol) 2-[(3R)-morpholin-3-yl]ethanol were added to 18 mg (0.45 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 15 h at 40° C.

The reaction mixture was poured into water, and extracted with ethyl acetate. The organic layer was dried over magnesium sulfate, and concentrated. The residue was purified by flash chromatography to yield 38 mg (40%) product as solid material.

¹H-NMR (400 MHz, DMSO-d₆), δ [ppm]=1.81 (2H), 2.70-2.78 (2H), 2.85-2.95 (1H), 3.11 (1H), 3.34-3.38 (1H), 3.65 (1H), 3.76 (1H), 4.59 (2H), 7.04 (1H), 7.27-7.38 (2H), 7.62-7.68 (2H), 7.73 (1H), 8.16 (2H).

LC-MS (Method 3): $R_t$=0.73 min; MS (ESIpos) m/z=365 [M+H]⁺.

Example 9

3-{[3-(1-Benzofuran-2-yl)imidazo[1,2-b]pyridazin-6-yl]oxy}-N-(propan-2-yl)propan-1-amine

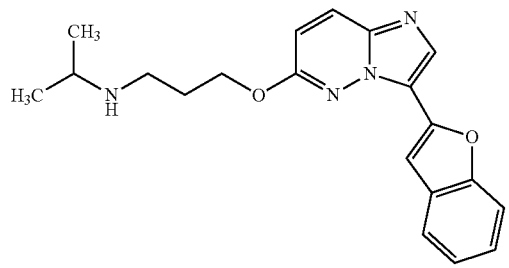 [SMILES: CC(C)NCCCOc1ccc2ncc(-c3cc4ccccc4o3)n2n1]

In an ice bath, 89 mg (0.74 mmol) 3-(propan-2-ylamino)propan-1-ol were added to 26 mg (0.65 mmol) sodium hydride (60% in mineral oil) in 5 mL anhydrous tetrahydrofurane. After 15 min of stirring in the ice bath, 100 mg (0.37 mmol) 3-(1-benzofur-2-yl)-6-chloroimidazo[1,2-b]pyridazine were added. The ice bath was removed and the reaction mixture was stirred for 16 h at room temperature.

The reaction mixture was poured into saturated aqueous ammonium chloride, and ethyl acetate was added. The resulting precipitate was filtered off, washed with water and ethyl acetate and dried in vacuum to give 124 mg (95%) of the product as solid material.

¹H-NMR (400 MHz, DMSO-d₆), δ [ppm]=1.23 (6H), 2.19-2.29 (2H), 3.11 (2H), 4.61 (2H), 7.03 (1H), 7.24-7.36 (2H), 7.60-7.65 (1H), 7.67 (1H), 7.71-7.76 (1H), 8.14-8.21 (2H).

LC-MS (Method 2): $R_t$=0.85 min; MS (ESIpos) m/z=351 [M+H]⁺.

Example 10

N-(2-{[3-(1-Benzofuran-2-yl)imidazo[1,2-b]pyridazin-6-yl]oxy}ethyl)propan-2-amine

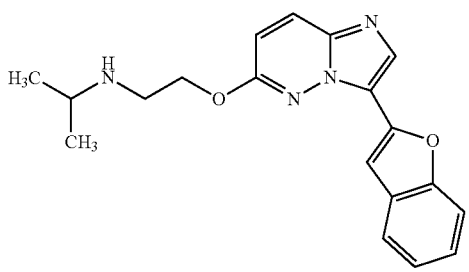 [SMILES: CC(C)NCCOc1ccc2ncc(-c3cc4ccccc4o3)n2n1]

In an ice bath, 78 mg (0.74 mmol) 2-(isopropylamino)ethan-1-ol were added to 26 mg (0.65 mmol) sodium hydride (60% in mineral oil) in 5 mL anhydrous tetrahydrofurane. After 15 min of stirring in the ice bath, 100 mg (0.37 mmol) 3-(1-benzofur-2-yl)-6-chloroimidazo[1,2-b]pyridazine were added. The ice bath was removed and the reaction mixture was stirred for 16 h at room temperature.

The reaction mixture was poured into saturated aqueous ammonium chloride, and extracted with ethyl acetate. The organic layer was dried over magnesium sulfate, and concentrated. The residue was purified by HPLC to yield 65 mg (46%) product as solid material.

$^1$H-NMR (300 MHz, DMSO-$d_6$), δ [ppm]=1.00 (6H), 3.00 (2H), 3.39 (1H), 4.53 (2H), 6.96-7.06 (1H), 7.23-7.36 (2H), 7.59-7.66 (2H), 7.68-7.74 (1H), 8.12-8.18 (2H).

LC-MS (Method 4): $R_t$=0.80 min; MS (ESIpos) m/z=337 [M+H]$^+$.

Example 11

3-(1-Benzofuran-2-yl)-6-[(2S)-morpholin-2-ylmethoxy]imidazo[1,2-b]pyridazine

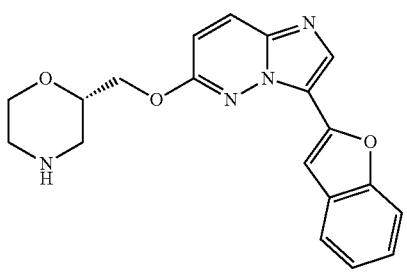 [SMILES: c1ccc2oc(-c3cnc4ccc(OC[C@@H]5CNCCO5)nn34)cc2c1]

In an ice bath, 355 mg (2.97 mmol) (S)-2-hydroxymethylmorpholine were added to 119 mg (2.97 mmol) sodium hydride (60% in mineral oil) in 6 mL anhydrous tetrahydrofurane. After 15 min of stirring in the ice bath, 200 mg (0.74 mmol) 3-(1-benzofur-2-yl)-6-chloroimidazo[1,2-b]pyridazine were added. The ice bath was removed and the reaction mixture was stirred for 24 h at room temperature.

The reaction mixture was poured into saturated aqueous ammonium chloride, and extracted with ethyl acetate. The organic layer was dried over magnesium sulfate, and concentrated to give 280 mg of a crude product. 49 mg of the crude product were purified by HPLC to yield 2 mg product as solid material.

$^1$H-NMR (300 MHz, DMSO-$d_6$), δ [ppm]=2.64-2.72 (3H), 2.94 (1H), 3.42-3.54 (1H), 3.72-3.89 (2H), 4.44 (2H), 7.06 (1H), 7.23-7.36 (2H), 7.60-7.65 (2H), 7.73 (1H), 8.12-8.20 (2H).

LC-MS (Method 3): $R_t$=0.76 min; MS (ESIpos) m/z=351 [M+H]$^+$.

Example 12

N-(2-{[3-(1-Benzofuran-2-yl)imidazo[1,2-b]pyridazin-6-yl]oxy}ethyl)-2,2-dimethylpropan-1-amine

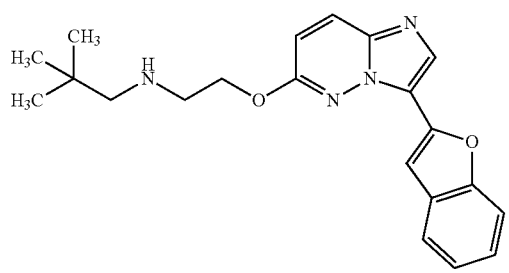 [SMILES: CC(C)(C)CNCCOc1ccc2ncc(-c3cc4ccccc4o3)n2n1]

In an ice bath, 68 mg (0.52 mmol) 2-[(2,2-dimetyhlpropyl)amino]ethanol were added to 18 mg (0.46 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 72 h at 40° C.

The reaction mixture was poured into water, and extracted with ethyl acetate. The organic layer was dried over magnesium sulfate, and concentrated. The residue was purified by HPLC to yield 50 mg (53%) product as solid material.

$^1$H-NMR (300 MHz, DMSO-$d_6$), δ [ppm]=0.84 (9H), 2.35 (2H), 3.01 (2H), 4.55 (2H), 7.03 (1H), 7.23-7.36 (2H), 7.62 (2H), 7.67-7.72 (1H), 8.11-8.17 (2H).

LC-MS (Method 4): $R_t$=0.89 min; MS (ESIpos) m/z=365 [M+H]$^+$.

Example 13

3-(1-Benzofuran-2-yl)-6-{2-[(3S)-morpholin-3-yl]ethoxy}imidazo[1,2-b]pyridazine

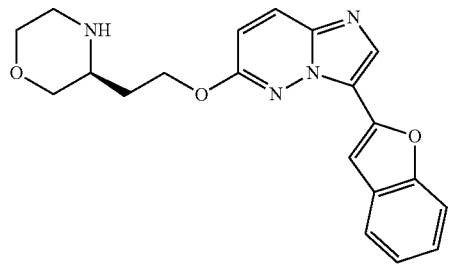 [SMILES: c1ccc2oc(-c3cnc4ccc(OCC[C@H]5COCCN5)nn34)cc2c1]

In an ice bath, 96 mg (0.52 mmol) (S)-2-(morpholin-3-yl)ethanol were added to 18 mg (0.46 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 15 h at 40° C.

The reaction mixture was poured into water, and extracted with ethyl acetate. The organic layer was dried over magnesium sulfate, and concentrated. The residue was purified by flash chromatography to yield 51 mg (54%) product as solid material.

¹H-NMR (400 MHz, DMSO-d$_6$), δ [ppm]=1.81 (2H), 2.73-2.80 (2H), 2.86-2.95 (1H), 3.12 (1H), 3.33-3.40 (1H), 3.65 (1H), 3.76 (1H), 4.59 (2H), 7.03 (1H), 7.27-7.38 (2H), 7.62-7.67 (2H), 7.70-7.75 (1H), 8.16 (2H).

LC-MS (Method 3): R$_t$=0.74 min; MS (ESIpos) m/z=365 [M+H]$^+$.

Example 14

6-(Azetidin-3-ylmethoxy)-3-(1-benzofuran-2-yl) imidazo[1,2-b]pyridazine

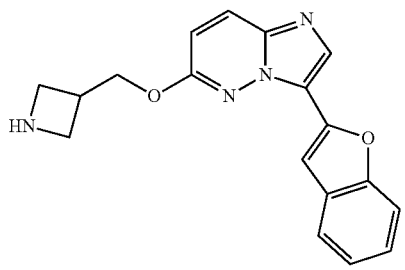 [SMILES: c1ccc2oc(-c3cnc4ccc(OCC5CNC5)nn34)cc2c1]

In an ice bath, 64 mg (0.52 mmol) 3-(hydroxymethyl) azetidine hydrochloride were added to 41 mg (1.04 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 72 h at 40° C.

The reaction mixture was poured into water, and extracted with ethyl acetate. The organic layer was dried over magnesium sulfate, and concentrated. The residue was purified by HPLC to yield 39 mg (46%) product as solid material.

¹H-NMR (300 MHz, DMSO-d$_6$), δ [ppm]=3.18 (1H), 3.50-3.60 (2H), 3.66-3.77 (2H), 4.63 (2H), 7.03 (1H), 7.22-7.37 (2H), 7.60-7.66 (2H), 7.70-7.76 (1H), 8.12-8.19 (2H).

LC-MS (Method 3): R$_t$=0.74 min; MS (ESIpos) m/z=321 [M+H]$^+$.

Example 15

3-(1-Benzofuran-2-yl)-6-{2-[(2S)-pyrrolidin-2-yl] ethoxy}imidazo[1,2-b]pyridazine

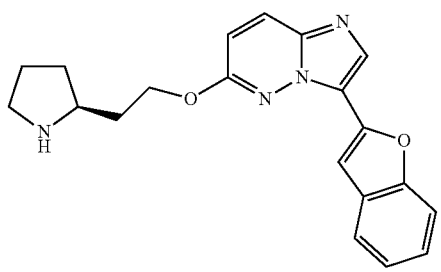 [SMILES: c1ccc2oc(-c3cnc4ccc(OCC[C@@H]5CCCN5)nn34)cc2c1]

Step 1: To 9.3 g (40.4 mmol) [(2S)-1-(tert.-butoxycarbonyl)pyrrolidin-2-yl]acetic acid in 116 mL tetrahydrofurane were added dropwise 40 mL of borane-dimethyl sulfide complex. The resulting mixture was stirred for 2 h at 80° C.

The mixture was carefully poured into saturated aqueous sodium hydrogencarbonate solution. The aqueous layer was extracted with methyl-tert.-butylether. The combined organic layers were washed with brine, dried over magnesium sulfate, and concentrated to give 6.2 g of a crude product which was used without further purification in step 2.

Step 2: In an ice bath, 1.37 g (6.39 mmol) of the crude product from step 1 were added to 224 mg (5.62 mmol) sodium hydride (60% in mineral oil) in 34 mL anhydrous tetrahydrofurane. After 15 min of stirring in the ice bath, 861 mg (3.19 mmol) 3-(1-benzofur-2-yl)-6-chloroimidazo[1,2-b]pyridazine were added. The ice bath was removed and the reaction mixture was stirred for 24 h at room temperature.

The reaction mixture was poured into saturated aqueous ammoniumchloride solution, and extracted with ethyl acetate. The combined organic phases were washed with brine, dried over magnesium sulfate, and concentrated. The obtained crude product (2.1 g) was used without further purification in step 3.

Step 3: To 1.4 g of the crude product from step 2 in 28 mL dichloromethane were added 4.9 mL of trifluoroacetic acid. The mixture was stirred for 1 h. Aqueous sodium hydroxide solution was added until the mixture reached basic pH. Brine was added and the mixture extracted with dichloromethane. The organic layer was separated, dried over magnesium sulfate and concentrated.

The residue was purified by HPLC to give 725 mg of the product as solid material.

1H-NMR (300 MHz, DMSO-d$_6$), δ [ppm]=1.57-1.72 (1H), 1.77-2.01 (2H), 2.11-2.32 (3H), 3.09-3.24 (2H), 3.64 (1H), 4.51-4.70 (2H), 7.02 (1H), 7.24-7.37 (2H), 7.60-7.66 (2H), 7.67-7.74 (1H), 8.13-8.23 (2H).

LC-MS (Method 1): R$_t$=0.82 min; MS (ESIpos) m/z=349 [M+H]$^+$.

Example 16

3-(1-Benzofuran-2-yl)-6-(piperidin-2-ylmethoxy) imidazo[1,2-b]pyridazine

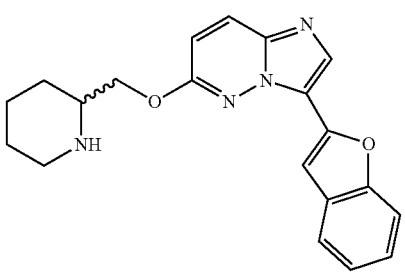 [SMILES: c1ccc2oc(-c3cnc4ccc(OCC5CCCCN5)nn34)cc2c1]

Step 1: In an ice bath, 1.95 g (8.9 mmol) tert.-butyl 2-(hydroxymethyl)piperidine-1-carboxylate were added to 313 mg (7.83 mmol) sodium hydride (60% in mineral oil) in 24 mL anhydrous tetrahydrofurane. After 15 min of stirring in the ice bath, 1.2 g (4.45 mmol) 3-(1-benzofur-2-yl)-6-chloroimidazo[1,2-b]pyridazine were added. The ice bath was removed and the reaction mixture was stirred for 4 days at room temperature.

The reaction mixture was poured into saturated aqueous ammoniumchloride solution, and extracted with ethyl acetate. The combined organic phases were washed with brine, dried over magnesium sulfate, and concentrated. The obtained crude product (1.65 g) was used without further purification in step 2.

Step 2: To the crude product from step 1 in 36 mL dichloromethane were added 8.9 mL of trifluoroacetic acid. The mixture was stirred for 3 h. Aqueous ammonia was added until the mixture reached basic pH. Brine was added and the mixture extracted with dichloromethane. The organic layer was separated, dried over magnesium sulfate and concentrated.

The residue was purified by HPLC to give 358 mg (23%) of the product as solid material.

$^1$H-NMR (500 MHz, DMSO-d$_6$), δ [ppm]=1.32-1.49 (3H), 1.62 (1H), 1.84 (2H), 2.66-2.71 (1H), 3.09 (1H), 3.17 (1H), 4.40-4.45 (1H), 4.46-4.51 (1H), 7.07 (1H), 7.30-7.35 (1H), 7.36-7.40 (1H), 7.65 (1H), 7.66-7.69 (1H), 7.74-7.78 (1H), 8.19-8.23 (2H).

LC-MS (Method 1): R$_t$=0.82 min; MS (ESIpos) m/z=349 [M+H]$^+$.

Example 17

N-(2-{[3-(1-Benzofuran-2-yl)imidazo[1,2-b]pyridazin-6-yl]oxy}ethyl)cyclopropanamine

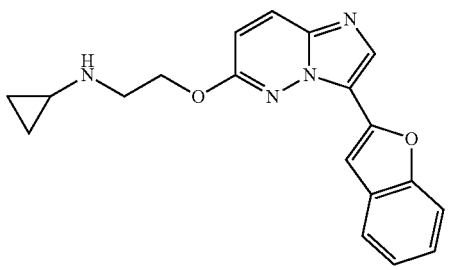 [SMILES: c1ccc2oc(-c3cnc4ccc(OCCNC5CC5)nn34)cc2c1]

In an ice bath, 77 mg (0.74 mmol) 2-(cyclopropylamino)ethan-1-ol were added to 26 mg (0.65 mmol) sodium hydride (60% in mineral oil) in 5 mL anhydrous tetrahydrofurane. After 15 min of stirring in the ice bath, 100 mg (0.37 mmol) 3-(1-benzofur-2-yl)-6-chloroimidazo[1,2-b]pyridazine were added. The ice bath was removed and the reaction mixture was stirred for 16 h at room temperature.

The reaction mixture was poured into saturated aqueous ammonium chloride, and extracted with ethyl acetate. The organic layer was dried over magnesium sulfate, and concentrated. The residue was digested in methanol to give 25 mg (20%) of the title compound as a solid material.

$^1$H-NMR (300 MHz, DMSO-d$_6$), δ [ppm]=0.70-0.94 (4H), 2.82 (1H), 3.58 (2H), 4.81 (2H), 7.04 (1H), 7.24-7.38 (2H), 7.61-7.67 (2H), 7.71 (1H), 8.17-8.25 (2H).

LC-MS (Method 2): R$_t$=0.82 min; MS (ESIpos) m/z=335 [M+H]$^+$.

Example 18

N-(2-{[3-(1-Benzofuran-2-yl)imidazo[1,2-b]pyridazin-6-yl]oxy}ethyl)-2-methylpropan-2-amine

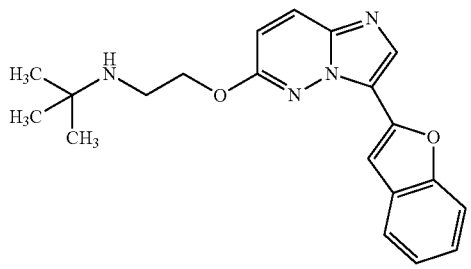 [SMILES: CC(C)(C)NCCOc1ccc2ncc(-c3cc4ccccc4o3)n2n1]

In an ice bath, 61 mg (0.52 mmol) 2-(tert.-butylamino)ethan-1-ol were added to 18.3 mg (0.46 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 72 h at 40° C.

The reaction mixture was poured into water, and extracted with ethyl acetate. The organic layer was dried over magnesium sulfate, and concentrated. The residue was digested in methyl-tert.-butylether to give 73 mg (80%) of the title compound as solid material.

$^1$H-NMR (400 MHz, DMSO-d$_6$), δ [ppm]=1.05 (9H), 2.96 (2H), 4.49 (2H), 7.02 (1H), 7.24-7.35 (2H), 7.62 (2H), 7.68-7.73 (1H), 8.11-8.16 (2H).

LC-MS (Method 4): R$_t$=0.82 min; MS (ESIpos) m/z=351 [M+H]$^+$.

Example 19

2-{[3-(1-Benzofuran-2-yl)imidazo[1,2-b]pyridazin-6-yl]oxy}-N-(propan-2-yl)propan-1-amine

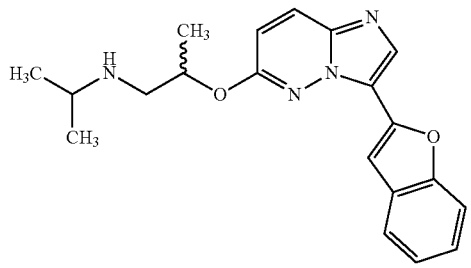 [SMILES: CC(C)NCC(C)Oc1ccc2ncc(-c3cc4ccccc4o3)n2n1]

In an ice bath, 61 mg (0.52 mmol) 1-(isopropylamino)propan-2-ol were added to 18.3 mg (0.46 mmol) sodium hydride (60% in mineral oil) in 4 mL anhydrous tetrahydrofurane. After 15 min of stirring in the ice bath, 70 mg (0.26 mmol) 3-(1-benzofur-2-yl)-6-chloroimidazo[1,2-b]pyridazine were added. The ice bath was removed and the reaction mixture was stirred for 16 h at 40° C.

The reaction mixture was poured into water, and extracted with ethyl acetate. The organic layer was dried over magnesium sulfate, and concentrated. The residue was purified by HPLC to give 52 mg (57%) of the title compound as solid material.

¹H-NMR (400 MHz, DMSO-d₆), δ [ppm]=0.97 (6H), 1.46 (3H), 2.74-2.84 (2H), 2.96 (1H), 5.25-5.35 (1H), 6.97 (1H), 7.24-7.35 (2H), 7.59 (1H), 7.62 (1H), 7.71 (1H), 8.14 (2H).

LC-MS (Method 4): R$_t$=0.84 min; MS (ESIpos) m/z=351 [M+H]⁺.

Example 20

3-(5-Chloro-1-benzofuran-2-yl)-6-[(2R)-morpholin-2-ylmethoxy]imidazo[1,2-b]pyridazine

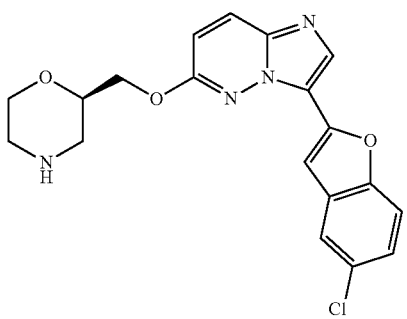 [SMILES: Clc1ccc2oc(-c3cnc4ccc(OC[C@H]5CNCCO5)nn34)cc2c1]

In an ice bath, 189 mg (1.58 mmol) (R)-2-hydroxymethylmorpholine were added to 63 mg (1.58 mmol) sodium hydride (60% in mineral oil) in 4 mL anhydrous tetrahydrofurane. After 15 min of stirring in the ice bath, 120 mg (0.4 mmol) 6-chloro-3-(5-chloro-1-benzofuran-2-yl)imidazo[1,2-b]pyridazine were added. The ice bath was removed and the reaction mixture was stirred for 16 h at room temperature.

The reaction mixture was poured into saturated aqueous ammonium chloride, and extracted with ethyl acetate. The organic layer was dried over magnesium sulfate, and concentrated. The residue was digested in methanol to give 15 mg (10%) of the title compound as a solid material.

1H-NMR (300 MHz, DMSO-d₆), δ [ppm]=2.57-2.72 (3H), 2.93 (1H), 3.48 (1H), 3.73-3.88 (2H), 4.42 (2H), 7.07 (1H), 7.33 (1H), 7.59 (1H), 7.66 (1H), 7.80 (1H), 8.13-8.19 (2H).

LC-MS (Method 3): R$_t$=0.88 min; MS (ESIpos) m/z=385 [M+H]⁺.

Example 21

3-(1-Benzofuran-2-yl)-6-[(2R)-pyrrolidin-2-ylmethoxy]imidazo[1,2-b]pyridazine

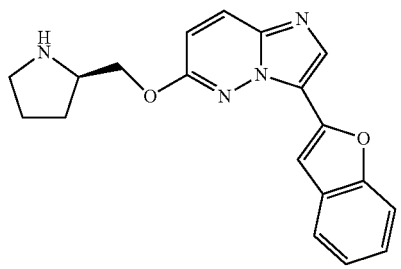 [SMILES: c1ccc2oc(-c3cnc4ccc(OC[C@H]5CCCN5)nn34)cc2c1]

In an ice bath, 5 g (49.4 mmol) (R)-2-(hydroxymethyl)pyrrolidine were added to 2.97 g (74.2 mmol) sodium hydride (60% in mineral oil) in 466 mL anhydrous tetrahydrofurane. After 15 min of stirring in the ice bath, 6.67 g (24.7 mmol) 3-(1-benzofur-2-yl)-6-chloroimidazo[1,2-b]pyridazine were added. The ice bath was removed and the reaction mixture was stirred for 16 h at 40° C.

The reaction mixture was carefully poured into brine, and extracted with ethyl acetate. The organic layer was dried over sodium sulfate, and concentrated. The residue was purified by flash chromatography to give 5.6 g (68%) of the title compound as a solid material.

¹H-NMR (300 MHz, DMSO-d₆), δ [ppm]=1.46-2.13 (4H), 2.73-2.89 (2H), 3.45-3.57 (1H), 4.26-4.33 (2H), 6.96-7.02 (1H), 7.29 (2H), 7.55 (1H), 7.61 (1H), 7.69-7.75 (1H), 8.12 (2H).

LC-MS (Method 3): R$_t$=0.79 min; MS (ESIpos) m/z=335 [M+H]⁺.

Example 22

3-(1-Benzofuran-2-yl)-6-(piperidin-3-yloxy)imidazo[1,2-b]pyridazine

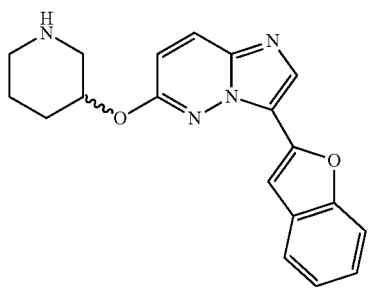 [SMILES: c1ccc2oc(-c3cnc4ccc(OC5CCCNC5)nn34)cc2c1]

In an ice bath, 5 g (49.4 mmol) piperidine-3-ol were added to 2.96 g (74.2 mmol) sodium hydride (60% in mineral oil) in 500 mL anhydrous tetrahydrofurane. After 15 min of stirring in the ice bath, 6.67 g (24.7 mmol) 3-(1-benzofur-2-yl)-6-chloroimidazo[1,2-b]pyridazine were added. The ice bath was removed and the reaction mixture was stirred for 12 hours at 40° C.

The reaction mixture was carefully poured into brine, and extracted with ethyl acetate. The organic layer was dried over sodium sulfate, and concentrated. The residue was digested in ethyl acetate to give 5.5 g (60%) of the title compound as a solid material.

¹H-NMR (400 MHz, DMSO-d₆), δ [ppm]=1.54-1.83 (3H), 2.23-2.32 (1H), 2.54-2.63 (1H), 2.75 (1H), 2.81-2.89 (1H), 3.33 (2H), 5.06 (1H), 7.00 (1H), 7.27-7.39 (2H), 7.54 (1H), 7.63-7.67 (1H), 7.72-7.76 (1H), 8.13-8.18 (2H).

LC-MS (Method 3): R$_t$=0.80 min; MS (ESIpos) m/z=335 [M+H]⁺.

Example 23

3-(1-Benzofuran-2-yl)-6-[(2S)-pyrrolidin-2-yl-methoxy]imidazo[1,2-b]pyridazine

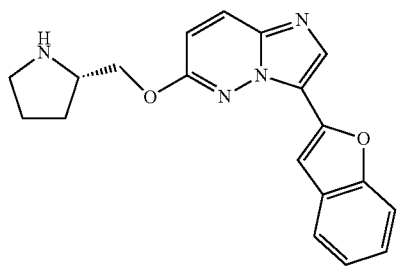 [SMILES: c1ccc2oc(-c3cnc4ccc(OC[C@@H]5CCCN5)nn34)cc2c1]

In an ice bath, 5 g (49.4 mmol) (S)-2-hydroxymethylpyrrolidine were added to 2.96 g (74.2 mmol) sodium hydride (60% in mineral oil) in 466 mL anhydrous tetrahydrofurane. After 15 min of stirring in the ice bath, 6.67 g (24.7 mmol) 3-(1-benzofur-2-yl)-6-chloroimidazo[1,2-b]pyridazine were added. The ice bath was removed and the reaction mixture was stirred for 12 h at 40° C.

The reaction mixture was carefully poured into brine, and extracted with ethyl acetate. The organic layer was dried over sodium sulfate, and concentrated. The residue was purified by flash chromatography to give 6.1 g (62%) of the title compound as solid material.

$^1$H NMR (300 MHz, DMSO-$d_6$) δ [ppm]=1.83-2.21 (4H), 3.40-3.56 (2H), 3.58-3.80 (2H), 4.17 (1H), 4.63-5.21 (1H), 7.03 (1H), 7.21-7.41 (2H), 7.49-7.79 (3H), 7.88-8.07 (2H).

LC-MS (Method 3): $R_t$=0.78 min; MS (ESIpos) m/z=335 [M+H]$^+$.

Example 24

1-{[3-(1-Benzofuran-2-yl)imidazo[1,2-b]pyridazin-6-yl]oxy}-N-methylpropan-2-amine

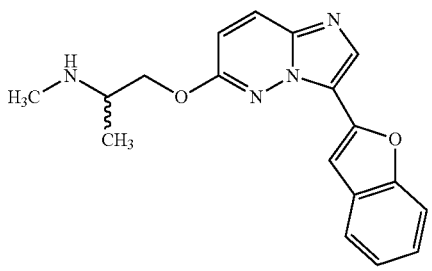 [SMILES: CNC(C)COc1ccc2ncc(-c3cc4ccccc4o3)n2n1]

At 0-5° C. 132 mg (1.48 mmol) 2-(methylamino)propan-1-ol were added to 59.3 mg (1.48 mmol) sodium hydride (60% in mineral oil) in 7.5 mL anhydrous DMF. After 5 min of stirring on the ice bath, 200 mg (0.74 mmol) 3-(1-benzofur-2-yl)-6-chloroimidazo[1,2-b]pyridazine were added. The ice bath was removed and it was stirred 1.5 h at room temperature.

The reaction mixture was poured into half saturated ammonium chloride solution, and extracted four times with ethyl acetate. The combined organic phases were washed with brine, dried over magnesium sulfate, and concentrated. The residue was purified by HPLC to yield 107.6 mg (45%) product.

$^1$H-NMR (300 MHz, DMSO-$d_6$), δ [ppm]=1.21 (3H), 2.43 (3H), 3.15-3.28 (1H), 4.46 (2H), 7.02 (1H), 7.23-7.37 (2H), 7.57-7.65 (2H), 7.69 (1H), 8.11-8.20 (2H).

LC-MS (Method 2): $R_t$=0.83 min; MS (ESIpos) m/z=323 [M+H]$^+$.

Example 25

3-(5-Chloro-1-benzofuran-2-yl)-6-{2-[(2S)-pyrrolidin-2-yl]ethoxy}imidazo[1,2-b]pyridazine

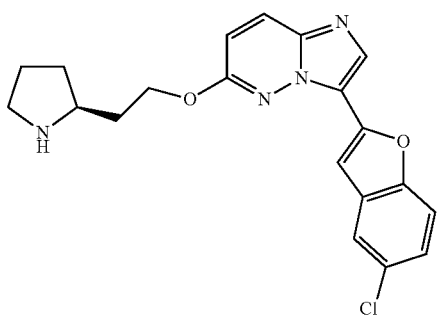 [SMILES: Clc1ccc2oc(-c3cnc4ccc(OCC[C@@H]5CCCN5)nn34)cc2c1]

Step 1: To 9.3 g (40.4 mmol) [(2S)-1-(tert.-butoxycarbonyl)pyrrolidin-2-yl]acetic acid in 116 mL tetrahydrofurane were added dropwise 40 mL of borane-dimethyl sulfide complex. The resulting mixture was stirred for 2 h at 80° C.

The mixture was carefully poured into saturated aqueous sodium hydrogencarbonate solution. The aqueous layer was extracted with methyl-tert.-butylether. The combined organic layers were washed with brine, dried over magnesium sulfate, and concentrated to give 6.2 g of a crude product which was used without further purification in step 2.

Step 2: In an ice bath, 150 mg (0.7 mmol) of the crude product from step 1 were added to 37 mg (0.93 mmol) sodium hydride (60% in mineral oil) in 6 mL anhydrous tetrahydrofurane. After 15 min of stirring in the ice bath, 189 mg (0.47 mmol) 3-(1-benzofur-2-yl)-6-chloroimidazo[1,2-b]pyridazine were added. The ice bath was removed and the reaction mixture was stirred for 18 h at room temperature.

The reaction mixture was poured into water, and extracted with ethyl acetate. The combined organic phases were dried over sodium sulfate, and concentrated. The obtained crude product (327 mg) was used without further purification in step 3.

Step 3: To 327 mg of the crude product from step 2 in 5.8 mL dichloromethane were added 1.3 mL of trifluoroacetic acid. The mixture was stirred for 1.5 h. Aqueous ammonia was added until the mixture reached basic pH. Brine was added and the mixture extracted with dichloromethane. The organic layer was separated, dried over magnesium sulfate and concentrated.

The residue was purified by HPLC to give 45 mg (17%) of the product as solid material.

$^1$H-NMR (300 MHz, DMSO-$d_6$), δ [ppm]=1.38-1.53 (1H), 1.67-1.86 (2H), 1.95-2.12 (3H), 2.87-3.06 (2H), 3.31-3.43 (2H), 4.60 (2H), 7.02-7.10 (1H), 7.33-7.41 (1H), 7.67 (2H), 7.79-7.85 (1H), 8.15-8.23 (2H).

LC-MS (Method 3): $R_t$=0.90 min; MS (ESIpos) m/z=383 [M+H]$^+$.

Example 26

2-{[3-(1-Benzofuran-2-yl)imidazo[1,2-b]pyridazin-6-yl]oxy}-N-methylpropan-1-amine

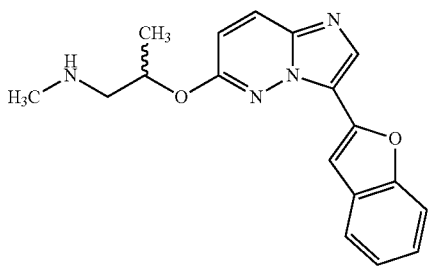 [SMILES: CNCC(C)Oc1ccc2ncc(-c3cc4ccccc4o3)n2n1]

At 0-5° C. 132 mg (1.48 mmol) 1-(methylamino)propan-2-ol were added to 59.3 mg (1.48 mmol) sodium hydride (60% in mineral oil) in 7.5 mL anhydrous DMF. After 5 min of stirring on the ice bath, 200 mg (0.74 mmol) 3-(1-benzofur-2-yl)-6-chloroimidazo[1,2-b]pyridazine were added. The ice bath was removed and it was stirred 1.5 h at room temperature.

The reaction mixture was poured into half saturated ammonium chloride solution, and extracted four times with ethyl acetate. The combined organic phases were washed with brine, dried over magnesium sulfate, and concentrated. The residue was purified by HPLC to yield 21 mg (9%) product.

$^1$H-NMR (400 MHz, DMSO-$d_6$), δ [ppm]=1.45 (3H), 2.36 (3H), 2.80-2.87 (1H), 2.90-2.98 (1H), 5.33-5.43 (1H), 6.96 (1H), 7.24-7.36 (2H), 7.58 (1H), 7.60-7.65 (1H), 7.68-7.74 (1H), 8.14 (2H).

LC-MS (Method 2): $R_t$=0.83 min; MS (ESIpos) m/z=323 [M+H]$^+$.

Example 27

Formic acid-N-(2-{[3-(1-benzofuran-2-yl)imidazo[1,2-b]pyridazin-6-yl]oxy}-2-phenylethyl)propan-2-amine (1:1)

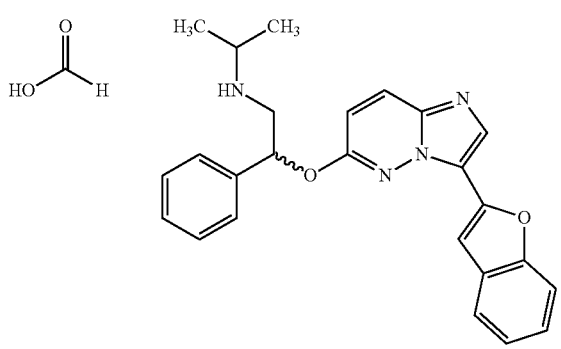 [SMILES: O=CO ; CC(C)NCC(Oc1ccc2ncc(-c3cc4ccccc4o3)n2n1)c1ccccc1]

At 0-5° C. 199 mg (1.11 mmol) 2-(isopropylamino)-1-phenylethanol were added to 44.5 mg (1.11 mmol) sodium hydride (60% in mineral oil) in 7.5 mL anhydrous DMF. After 5 min of stirring on the ice bath, 150 mg (0.56 mmol) 3-(1-benzofur-2-yl)-6-chloroimidazo[1,2-b]pyridazine were added. The ice bath was removed and it was stirred 3 h at room temperature. The reaction mixture was poured into half saturated ammonium chloride solution, and extracted four times with ethyl acetate. The combined organic phases were washed with brine, dried over magnesium sulfate, and concentrated. The residue was purified by HPLC to yield 105 mg (41%) product.

$^1$H-NMR (400 MHz, DMSO-$d_6$), δ [ppm]=1.05 (6H), 2.86-2.97 (1H), 3.00-3.07 (1H), 3.18-3.26 (1H), 6.11-6.16 (1H), 7.17 (1H), 7.25-7.44 (6H), 7.61 (3H), 7.75-7.81 (2H), 8.11 (1H), 8.17-8.24 (2H).

LC-MS (Method 2): $R_t$=0.98 min; MS (ESIpos) m/z=413 [M+H]$^+$.

Example 28

N-(2-{[3-(1-Benzofuran-2-yl)imidazo[1,2-b]pyridazin-6-yl]oxy}-2-phenylethyl)-2-methylpropan-1-amine

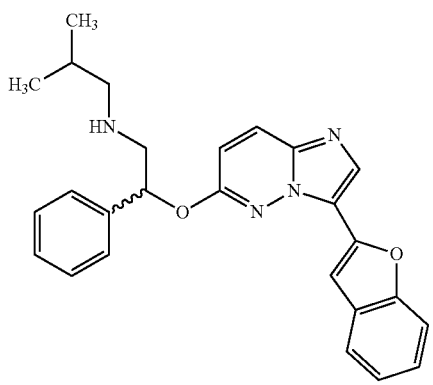 [SMILES: CC(C)CNCC(Oc1ccc2ncc(-c3cc4ccccc4o3)n2n1)c1ccccc1]

At 0-5° C. 215 mg (1.11 mmol) 2-(isobutylamino)-1-phenylethanol were added to 44.5 mg (1.11 mmol) sodium hydride (60% in mineral oil) in 7.5 mL anhydrous DMF. After 5 min of stirring on the ice bath, 150 mg (0.56 mmol) 3-(1-benzofur-2-yl)-6-chloroimidazo[1,2-b]pyridazine were added. The ice bath was removed and it was stirred 1.5 h at room temperature. The reaction mixture was poured into half saturated ammonium chloride solution, and extracted four times with ethyl acetate. The combined organic phases were washed with brine, dried over magnesium sulfate, and concentrated. The residue was purified by HPLC to yield 101 mg (43%) product.

$^1$H-NMR (400 MHz, DMSO-$d_6$), δ [ppm]=0.84 (6H), 1.61-1.72 (1H), 2.45 (2H), 2.93-3.00 (1H), 3.12-3.20 (1H), 6.09-6.15 (1H), 7.16 (1H), 7.24-7.43 (6H), 7.60 (3H), 7.74-7.79 (1H), 8.10 (1H), 8.18 (1H).

LC-MS (Method 2): $R_t$=1.11 min; MS (ESIpos) m/z=427 [M+H]$^+$.

Example 29

(-)-2-{[3-(1-Benzofuran-2-yl)imidazo[1,2-b]pyridazin-6-yl]oxy}-N-methyl-2-phenylethanamine

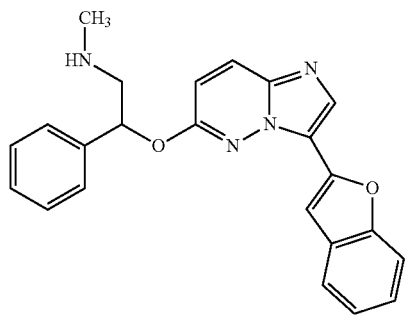 [SMILES: CNCC(Oc1ccc2ncc(-c3cc4ccccc4o3)n2n1)c1ccccc1]

At 0-5° C. 56 mg (0.371 mmol) racemic 2-(methylamino)-1-phenylethanol were added to 7.4 mg (0.185 mmol) sodium hydride (60% in mineral oil) in 2.5 mL anhydrous DMF. After 30 min of stirring on the ice bath, 50 mg (0.185 mmol) 3-(1-benzofur-2-yl)-6-chloroimidazo[1,2-b]pyridazine were added. The ice bath was removed and it was stirred 3 h at room temperature.

The reaction mixtures were poured into half saturated ammonium chloride solution, and extracted four times with ethyl acetate. The combined organic phases were washed with brine, dried over magnesium sulfate, and concentrated. The residue was purified by HPLC to yield 44 mg (62%) product.

LC-MS (Method 2): $R_t$=0.99 min; MS (ESIpos) m/z=385 [M+H]$^+$.

The enantiomers were separated by chiral HPLC (Chiralpak IA 5 μm, 250×30 mm, Hexan/Ethanol 90:10+0.1% diethylamine, 40 mL/min).

Peak1: 20 mg, α=−432.2° (1.00; CHCl$_3$)

$^1$H-NMR (300 MHz, CHLOROFORM-d), δ [ppm]=2.55 (3H), 3.04 (1H), 3.28 (1H), 6.16 (1H), 6.90 (1H), 7.18 (1H), 7.24-7.35 (3H), 7.40 (2H), 7.48-7.57 (3H), 7.63 (1H), 7.90 (1H), 8.09 (1H).

Example 30

N-(2-{[3-(1-Benzofuran-2-yl)imidazo[1,2-b]pyridazin-6-yl]oxy}-2-phenylethyl)-2,2-dimethyl-propan-1-amine

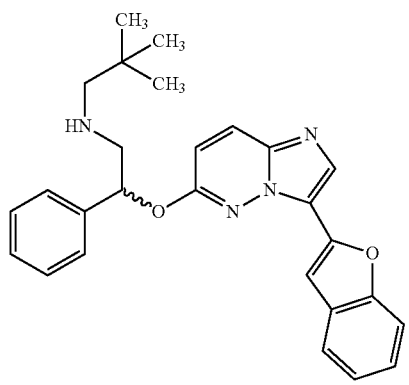 [SMILES: CC(C)(C)CNCC(Oc1ccc2ncc(-c3cc4ccccc4o3)n2n1)c1ccccc1]

At 0-5° C. 361.6 mg (1.48 mmol) 2-[(2,2-dimethylpropyl)amino]-1-phenylethanol hydrochloride were added to 118.6 mg (2.97 mmol) sodium hydride (60% in mineral oil) in 10 mL anhydrous DMF. After 5 min of stirring on the ice bath, 200 mg (0.74 mmol) 3-(1-benzofur-2-yl)-6-chloroimidazo[1,2-b]pyridazine were added. The ice bath was removed and it was stirred 1.5 h at room temperature. The reaction mixture was poured into half saturated ammonium chloride solution, and extracted four times with ethyl acetate. The combined organic phases were washed with brine, dried over magnesium sulfate, and concentrated. The residue was purified by HPLC to yield 186 mg (57%) product.

$^1$H-NMR (400 MHz, DMSO-d$_6$), δ [ppm]=0.83 (9H), 2.41 (2H), 2.94-3.02 (1H), 3.14-3.23 (1H), 6.09-6.16 (1H), 7.17 (1H), 7.24-7.44 (6H), 7.60 (3H), 7.74-7.79 (1H), 8.10 (1H), 8.19 (1H).

LC-MS (Method 2): $R_t$=1.03 min; MS (ESIpos) m/z=441 [M+H]$^+$.

Example 31

3-(1-Benzofuran-2-yl)-6-[(3R)-pyrrolidin-3-yloxy]imidazo[1,2-b]pyridazine

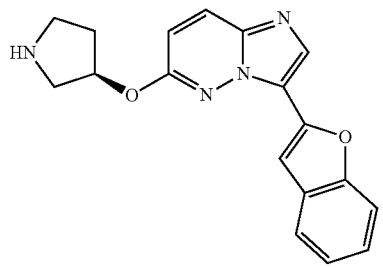 [SMILES: c1ccc2oc(-c3cnc4ccc(O[C@@H]5CCNC5)nn34)cc2c1]

At 0-5° C. 1.551 g (17.80 mmol) (3R)-pyrrolidin-3-ol were added to 712 mg (17.80 mmol) sodium hydride (60% in mineral oil) in 60 mL anhydrous DMF. After 5 min of stirring on the ice bath, 2.4 g (8.90 mmol) 3-(1-benzofur-2-yl)-6-chloroimidazo[1,2-b]pyridazine were added. The ice bath was removed and it was stirred over night at room temperature. The reaction mixture was poured into saturated ammonium chloride solution, and extracted ten times with 100 mL chloroform. The combined organic phases were dried over magnesium sulfate, and concentrated. The crude material was combined with a second batch with the same amount under the same conditions. The residue was purified on silica gel with dichloromethane and methanol. The collected fractions were concentrated and digested in 2-isopropoxypropane. The solid was filtered off, washed with diethyl ether and dried under vacuum over the weekend at room temperature to yield 2.55 g (43%) product.

$^1$H-NMR (400 MHz, DMSO-d$_6$), δ [ppm]=1.90-1.99 (1H), 2.15-2.26 (1H), 2.79-2.88 (1H), 2.89-2.98 (1H), 2.99-3.05 (1H), 3.22-3.26 (1H, and water signal), 5.50-5.56 (1H), 6.97 (1H), 7.24-7.35 (2H), 7.58-7.65 (2H), 7.74 (1H), 8.08-8.17 (2H).

LC-MS (Method 2): $R_t$=0.81 min; MS (ESIpos) m/z=321 [M+H]$^+$.

[α]=62.5°, (methanol, 0.28)

Example 32

3-(1-Benzofuran-2-yl)-6-[(3R)-piperidin-3-yloxy]imidazo[1,2-b]pyridazine

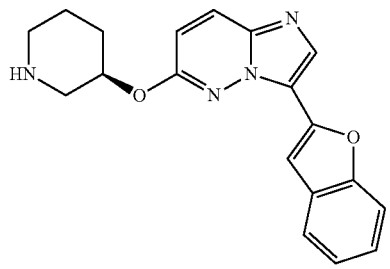 [SMILES: c1ccc2oc(-c3cnc4ccc(O[C@@H]5CCCNC5)nn34)cc2c1]

At 0-5° C. 200 mg (1.45 mmol) (3R)-piperidin-3-ol hydrochloride were added to 116.3 mg (2.91 mmol) sodium hydride (60% in mineral oil) in 7 mL anhydrous DMF. After 5 min of stirring on the ice bath, 196 mg (0.73 mmol) 3-(1-benzofur-2-yl)-6-chloroimidazo[1,2-b]pyridazine were added. The ice bath was removed and it was stirred over night at room temperature. The reaction mixture was poured into saturated ammonium chloride solution, and extracted four times with ethyl acetate. The combined organic phases were washed twice with brine, dried over magnesium sulfate, and concentrated. The crude material was treated with 5 mL DMSO. The solid was filtered off and washed with water. It was dried at 45° C. and vacuum yielding 155 mg (63%) product.

$^1$H-NMR (400 MHz, CHLOROFORM-d), δ [ppm]=1.69 (1H), 1.85-2.03 (2H), 2.22-2.32 (1H), 2.84-2.92 (1H), 2.92-3.00 (1H), 3.10 (1H), 3.35 (1H), 5.14-5.22 (1H), 6.80 (1H), 7.24-7.36 (2H, and chloroform signal), 7.45 (1H), 7.55 (1H), 7.65 (1H), 7.90 (1H), 8.18 (1H).

LC-MS (Method 2): $R_t$=0.78 min; MS (ESIpos) m/z=335 [M+H]$^+$.

Example 33

3-(4-Fluoro-1-benzofuran-2-yl)-6-[(2R)-morpholin-2-ylmethoxy]imidazo[1,2-b]-pyridazine

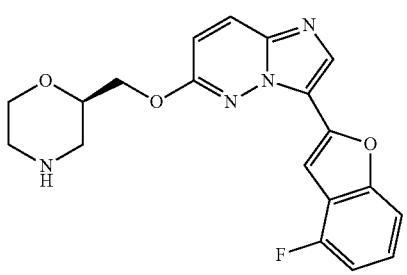 [SMILES: Fc1cccc2oc(-c3cnc4ccc(OC[C@H]5CNCCO5)nn34)cc12]

In an ice bath, 51 mg (0.43 mmol) (2R)-morpholin-2-ylmethanol were added to 17 mg (0.43 mmol) sodium hydride (60% in mineral oil) in 4 mL anhydrous tetrahydrofurane. After 15 min of stirring in the ice bath, 74 mg (0.22 mmol) 6-chloro-3-(4-fluoro-1-benzofuran-2-yl)imidazo[1,2-b]pyridazine were added. The ice bath was removed and the reaction mixture was stirred for 18 h at 40° C.

The reaction mixture was carefully poured into water, and extracted with ethyl acetate. The organic layer was dried over sodium sulfate, and concentrated. The residue was purified by HPLC to give 49 mg (55%) of the title compound as solid material.

$^1$H-NMR (300 MHz, DMSO-d$_6$), δ [ppm]=2.54-2.72 (3H), 2.94 (1H), 3.42-3.54 (1H), 3.77 (1H), 3.82-3.91 (1H), 4.43 (2H), 7.03-7.17 (2H), 7.35 (1H), 7.52 (1H), 7.58 (1H), 8.14-8.20 (2H).

LC-MS (Method 4): $R_t$=0.81 min; MS (ESIpos) m/z=369 [M+H]$^+$.

Example 34

3-(5-Fluoro-1-benzofuran-2-yl)-6-[(2R)-morpholin-2-ylmethoxy]imidazo[1,2-b]-pyridazine

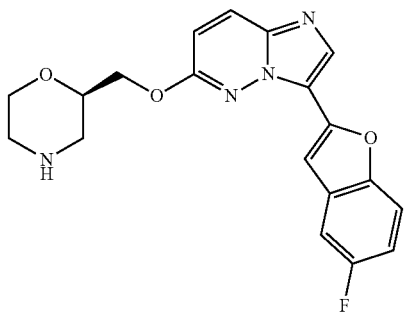 [SMILES: Fc1ccc2oc(-c3cnc4ccc(OC[C@H]5CNCCO5)nn34)cc2c1]

In an ice bath, 33 mg (0.29 mmol) (2R)-morpholin-2-ylmethanol were added to 12 mg (0.29 mmol) sodium hydride (60% in mineral oil) in 4 mL anhydrous tetrahydrofurane. After 15 min of stirring in the ice bath, 69 mg (0.14 mmol) 6-chloro-3-(5-fluoro-1-benzofuran-2-yl)imidazo[1,2-b]pyridazine were added. The ice bath was removed and the reaction mixture was stirred for 18 h at 40° C.

The reaction mixture was carefully poured into saturated aqueous ammonium chloride solution, and extracted with ethyl acetate. The organic layer was dried over sodium sulfate, and concentrated. The residue was purified by HPLC to give 14 mg (24%) of the title compound as solid material.

$^1$H-NMR (400 MHz, DMSO-d$_6$), δ [ppm]=2.65-2.77 (3H), 2.99 (1H), 3.47-3.55 (1H), 3.80 (1H), 3.83-3.91 (1H), 4.44 (2H), 7.04-7.10 (1H), 7.15 (1H), 7.53 (1H), 7.60 (1H), 7.65 (1H), 8.14-8.19 (2H).

LC-MS (Method 4): $R_t$=0.82 min; MS (ESIpos) m/z=369 [M+H]$^+$.

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science a Technology 1998, 52(5), 238-311; Strickley, R. G "Parenteral Formulations of Small Molecule Therapeutics Marketed in the United States (1999)-Part-1" PDA Journal of Pharmaceutical Science a Technology 1999, 53(6), 324-349; and Nema, S. et al., "Excipients and Their Use in Injectable Products" PDA Journal of Pharmaceutical Science a Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC\text{—}CClF_2$ and $CClF_3$) air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate) flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 min.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 min.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The term "chemotherapeutic anti-cancer agents", includes but is not limited to
131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon.alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

A compound of general formula (I) as defined herein can optionally be administered in combination with one or more of the following: ARRY-162, ARRY-300, ARRY-704, AS-703026, AZD-5363, AZD-8055, BEZ-235, BGT-226, BKM-120, BYL-719, CAL-101, CC-223, CH-5132799, deforolimus, E-6201, enzastaurin, GDC-0032, GDC-0068, GDC-0623, GDC-0941, GDC-0973, GDC-0980, GSK-2110183, GSK-2126458, GSK-2141795, MK-2206, novolimus, OSI-027, perifosine, PF-04691502, PF-05212384, PX-866, rapamycin, RG-7167, RO-4987655, RO-5126766, selumetinib, TAK-733, trametinib, triciribine, UCN-01, WX-554, XL-147, XL-765, zotarolimus, ZSTK-474.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit MKNK-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays:

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

MKNK1 Kinase Assay

MKNK1-inhibitory activity of compounds of the present invention was quantified employing the MKNK1 TR-FRET assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nL of a 100fold concentrated solution of the test compound in DMSO was pipetted into a black low volume 384well microtiter plate (Greiner Bio-One, Frickenhausen, Germany), 2 µL of a solution of MKNK1 in aqueous assay buffer [50 mM HEPES pH 7.5, 5 mM magnesium chloride, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (0.1 µM=>final conc. in the 5 µL assay volume is 0.06 µM) in assay buffer and the resulting mixture was incubated for a reaction time of 45 min at 22° C. The concentration of MKNK1 was adjusted depending of the activity of the enzyme lot and was chosen appropriate to have the assay in the linear range, typical concentrations were in the range of 0.05 µg/mL. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit.

TABLE 1

MKNK1 $IC_{50}$s

| Example | MKNK1 $IC_{50}$ [nM] |
| --- | --- |
| 1 | 4 |
| 3 | 4 |
| 4 | 4 |
| 6 | 7 |
| 8 | 6 |
| 9 | 7 |
| 10 | 8 |
| 11 | 12 |
| 12 | 11 |
| 13 | 9 |
| 15 | 12 |
| 16 | 16 |
| 17 | 8 |
| 18 | 24 |
| 19 | 16 |
| 21 | 15 |
| 22 | 25 |
| 23 | 25 |
| 25 | 39 |
| 27 | 36 |
| 28 | 59 |
| 29 | 98 |
| 30 | 227 |
| 31 | 22 |
| 32 | 28 |
| 33 | 10 |
| 34 | 10 |

MKNK1 Kinase High ATP Assay

MKNK1-inhibitory activity at high ATP of compounds of the present invention after their preincubation with MKNK1 was quantified employing the TR-FRET-based MKNK1 high ATP assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used, which can be purchased e.g. from the company Biosyntan (Berlin-Buch, Germany).

For the assay 50 nL of a 100fold concentrated solution of the test compound in DMSO was pipetted into a black low volume 384well microtiter plate (Greiner Bio-One, Frickenhausen, Germany), 2 µL of a solution of MKNK1 in aqueous assay buffer [50 mM HEPES pH 7.5, 5 mM magnesium chloride, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 3.3 mM=>final conc. in the 5 μL assay volume is 2 mM) and substrate (0.1 μM=>final conc. in the 5 μL assay volume is 0.06 μM) in assay buffer and the resulting mixture was incubated for a reaction time of 30 min at 22° C. The concentration of MKNK1 was adjusted depending of the activity of the enzyme lot and was chosen appropriate to have the assay in the linear range, typical concentrations were in the range of 0.003 μg/mL. The reaction was stopped by the addition of 5 μL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated by a 4 parameter fit.

TABLE 2

| MKNK1 high $IC_{50}$s | |
|---|---|
| Example | MKNK1 high ATP $IC_{50}$ [nM] |
| 1 | 6 |
| 2 | 11 |
| 3 | 12 |
| 4 | 13 |
| 5 | 18 |
| 6 | 18 |
| 7 | 19 |
| 8 | 20 |
| 9 | 20 |
| 10 | 23 |
| 11 | 24 |
| 12 | 25 |
| 13 | 25 |
| 14 | 27 |
| 15 | 30 |
| 16 | 32 |
| 17 | 36 |
| 18 | 37 |
| 19 | 38 |
| 20 | 41 |
| 21 | 44 |
| 22 | 53 |
| 23 | 53 |
| 24 | 55 |
| 25 | 91 |

TABLE 2-continued

| MKNK1 high $IC_{50}$s | |
|---|---|
| Example | MKNK1 high ATP $IC_{50}$ [nM] |
| 26 | 93 |
| 27 | 75 |
| 28 | 114 |
| 29 | 124 |
| 30 | 239 |
| 31 | 49 |
| 32 | 53 |
| 33 | 15 |
| 34 | 11 |

CDK2/CycE Kinase Assay

CDK2/CycE-inhibitory activity of compounds of the present invention was quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nL of a 100fold concentrated solution of the test compound in DMSO was pipetted into a black low volume 384well microtiter plate (Greiner Bio-One, Frickenhausen, Germany), 2 μL of a solution of CDK2/CycE in aqueous assay buffer [50 mM Tris/hydrochloric acid pH 8.0, 10 mM magnesium chloride, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 16.7 μM=>final conc. in the 5 μL assay volume is 10 μM) and substrate (1.25 μM=>final conc. in the 5 μL assay volume is 0.75 μM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL. The reaction was stopped by the addition of 5 μL of a solution of TR-FRET detection reagents (0.2 μM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/sodium hydroxide pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit.

PDGFRl3 Kinase Assay

PDGFRl3 inhibitory activity of compounds of the present invention was quantified employing the PDGFRl3 HTRF assay as described in the following paragraphs.

As kinase, a GST-His fusion protein containing a C-terminal fragment of human PDGFRβ (amino acids 561-1106, expressed in insect cells [SF9] and purified by affinity chromatography, purchased from Proqinase [Freiburg i.Brsg., Germany] was used. As substrate for the kinase reaction the biotinylated poly-Glu,Tyr (4:1) copolymer (#61GT0BLA) from Cis Biointernational (Marcoule, France) was used.

For the assay 50 nL of a 100fold concentrated solution of the test compound in DMSO was pipetted into a black low volume 384well microtiter plate (Greiner Bio-One, Frickenhausen, Germany), 2 μL of a solution of PDGFRβ in aqueous assay buffer [50 mM HEPES/sodium hydroxide pH 7.5, 10 mM magnesium chloride, 2.5 mM dithiothreitol, 0.01% (v/v) Triton-X100 (Sigma)] were added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 16.7 μM=>final conc. in the 5 μL assay volume is 10 μM) and substrate (2.27 μg/mL=>final conc. in the 5 μL assay volume is 1.36 μg/mL [~30 nM]) in assay buffer and the resulting mixture was incubated for a reaction time of 25 min at 22° C. The concentration of PDGFRβ in the assay was adjusted depending of the activity of the enzyme lot and was chosen appropriate to have the assay in the linear range, typical enzyme concentrations were in the range of about 125 pg/μL (final conc. in the 5 μL assay volume). The reaction was stopped by the addition of 5 μL of a solution of HTRF detection reagents (200 nM streptavidine-XLent [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/sodium hydroxide pH 7.5).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100fold conc. stock solutions by serial 1:3 dilutions) in duplicate values for each concentration and $IC_{50}$ values were calculated by a 4 parameter fit.

Fyn Kinase Assay

C-terminally His6-tagged human recombinant kinase domain of the human T-Fyn expressed in baculovirus infected insect cells (purchased from Invitrogen, P3042) was used as kinase. As substrate for the kinase reaction the biotinylated peptide biotin-KVEKIGEGTYGW (C-terminus in amid form) was used which can be purchased e.g. form the company Biosynthan GmbH (Berlin-Buch, Germany).

For the assay 50 nL of a 100fold concentrated solution of the test compound in DMSO was pipetted into a black low volume 384well microtiter plate (Greiner Bio-One, Frickenhausen, Germany), 2 μL of a solution of T-Fyn in aqueous assay buffer [25 mM Tris/hydrochloric acid pH 7.2, 25 mM magnesium chloride, 2 mM dithiothreitol, 0.1% (w/v) bovine serum albumin, 0.03% (v/v) Nonidet-P40 (Sigma)]. were added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 16.7 μM=>final conc. in the 5 μL assay volume is 10 μM) and substrate (2 μM=>final conc. in the 5 μL assay volume is 1.2 μM) in assay buffer and the resulting mixture was incubated for a reaction time of 60 min at 22° C. The concentration of Fyn was adjusted depending of the activity of the enzyme lot and was chosen appropriate to have the assay in the linear range, typical concentration was 0.13 nM. The reaction was stopped by the addition of 5 μL of a solution of HTRF detection reagents (0.2 μM streptavidine-XL [Cisbio Bioassays, Codolet, France) and 0.66 nM PT66-Eu-Chelate, an europium-chelate labelled anti-phospho-tyrosine antibody from Perkin Elmer [instead of the PT66-Eu-chelate PT66-Tb-Cryptate from Cisbio Bioassays can also be used]) in an aqueous EDTA-solution (125 mM EDTA, 0.2% (w/v) bovine serum albumin in 50 mM HEPES/sodium hydroxide pH 7.0).

The resulting mixture was incubated 1 h at 22° C. to allow the binding of the biotinylated phosphorylated peptide to the streptavidine-XL and the PT66-Eu-Chelate. Subsequently the amount of phosphorylated substrate was evaluated by measurement of the resonance energy transfer from the PT66-Eu-Chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compounds were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100fold conc. stock solutions by serial 1:3 dilutions) in duplicate values for each concentration and $IC_{50}$ values were calculated by a 4 parameter fit.

Flt4 Kinase Assay

Flt4 inhibitory activity of compounds of the present invention was quantified employing the Flt4 TR-FRET assay as described in the following paragraphs.

As kinase, a GST-His fusion protein containing a C-terminal fragment of human Flt4 (amino acids 799-1298, expressed in insect cells [SF9] and purified by affinity chromatography, purchased from Proqinase [Freiburg i.Brsg., Germany] was used. As substrate for the kinase reaction the biotinylated peptide Biotin- Ahx-GGEEEEY-FELVKKKK (C-terminus in amide form, purchased from Biosyntan, Berlin-Buch, Germany) was used.

For the assay 50 nL of a 100fold concentrated solution of the test compound in DMSO was pipetted into a black low volume 384well microtiter plate (Greiner Bio-One, Frickenhausen, Germany), 2 µL of a solution of Flt4 in aqueous assay buffer [25 mM HEPES pH 7.5, 10 mM magnesium chloride, 2 mM dithiothreitol, 0.01% (v/v) Triton-X100 (Sigma), 0.5 mM EGTA, and 5 mM β-phospho-glycerol] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture was incubated for a reaction time of 45 min at 22° C. The concentration of Flt4 in the assay was adjusted depending of the activity of the enzyme lot and was chosen appropriate to have the assay in the linear range, typical enzyme concentrations were in the range of about 120 pg/µL (final conc. in the 5 µL assay volume). The reaction was stopped by the addition of 5 µL of a solution of HTRF detection reagents (200 nM streptavidine-XL665 [Cis Biointernational] and 1 nM PT66-Tb-Cryptate, an terbium-cryptate labelled anti-phospho-tyrosine antibody from Cisbio Bioassays (Codolet, France) in an aqueous EDTA-solution (50 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100fold conc. stock solutions by serial 1:3 dilutions) in duplicate values for each concentration and $IC_{50}$ values were calculated by a 4 parameter fit.

TrkA Kinase Assay

TrkA inhibitory activity of compounds of the present invention was quantified employing the TrkA HTRF assay as described in the following paragraphs.

As kinase, a GST-His fusion protein containing a C-terminal fragment of human TrkA (amino acids 443-796, expressed in insect cells [SF9] and purified by affinity chromatography, purchased from Proqinase [Freiburg i.Brsg., Germany] was used. As substrate for the kinase reaction the biotinylated poly-Glu, Tyr (4:1) copolymer (#61GT0BLA) from Cis Biointernational (Marcoule, France) was used.

For the assay 50 nL of a 100fold concentrated solution of the test compound in DMSO was pipetted into a black low volume 384well microtiter plate (Greiner Bio-One, Frickenhausen, Germany), 2 µL of a solution of TrkA in aqueous assay buffer [8 mM MOPS/hydrochloric acid pH 7.0, 10 mM magnesium chloride, 1 mM dithiothreitol, 0.01% (v/v) NP-40 (Sigma), 0.2 mM EDTA] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (2.27 µg/mL=>final conc. in the 5 µL assay volume is 1.36 µg/mL [~30 nM]) in assay buffer and the resulting mixture was incubated for a reaction time of 60 min at 22° C. The concentration of TrkA in the assay was adjusted depending of the activity of the enzyme lot and was chosen appropriate to have the assay in the linear range, typical enzyme concentrations were in the range of about 20 pg/µL (final conc. in the 5 µL assay volume). The reaction was stopped by the addition of 5 µL of a solution of HTRF detection reagents (30 nM streptavidine-XL665 [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/sodium hydroxide pH 7.5).

The resulting mixture was incubated 1 h at 22° C. to allow the binding of the biotinylated phosphorylated peptide to the streptavidine-XL665 and the PT66-Eu-Chelate. Subsequently the amount of phosphorylated substrate was evaluated by measurement of the resonance energy transfer from the PT66-Eu-Chelate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100fold conc. stock solutions by serial 1:3 dilutions) in duplicate values for each concentration and $IC_{50}$ values were calculated by a 4 parameter fit.

AlphaScreen SureFire eIF4E Ser209 Phosphorylation Assay

The AlphaScreen SureFire eIF4E Ser209 phoshorylation assay is used to measure the phosphorylation of endogenous eIF4E in cellular lysates. The AlphaScreen SureFire technology allows the detection of phosphorylated proteins in cellular lysates. In this assay, sandwich antibody complexes, which are only formed in the presence of the analyte (p-eIF4E Ser209), are captured by AlphaScreen donor and acceptor beads, bringing them into close proximity. The excitation of the donor bead provokes the release of singlet oxygen molecules that triggers a cascade of energy transfer in the Acceptor beads, resulting in the emission of light at 520-620 nm.

Surefire EIF4e Alphascreen in A549 Cells with 20% FCS Stimulation

For the assay the AlphaScreen SureFire p-eIF4E Ser209 10K Assay Kit and the AlphaScreen ProteinA Kit (for 10K assay points) both from Perkin Elmer were used.

On day one 50.000 A549 cells were plated in a 96-well plate in 100 µL per well in growth medium (DMEM/Hams' F12 with stable glutamine, 10% FCS) and incubated at 37° C. After attachment of the cells, medium was changed to starving medium (DMEM, 0.1% FCS, without glucose, with glutamine, supplemented with 5 g/L maltose). On day two, test compounds were serially diluted in 50 µL starving medium with a final DMSO concentration of 1% and were added to A549 cells in test plates at a final concentration range from as high 10 µM to as low 10 nM depending on the activities of the tested compounds. Treated cells were incubated at 37° C. for 2 h. 37 ul FCS was added to the wells (=final FCS concentration 20%) for 20 min. Then medium was removed and cells were lysed by adding 50 µL lysis buffer. Plates were then agitated on a plate shaker for 10 min. After 10 min lysis time, 4 µL of the lysate is transferred to a 384well plate (Proxiplate from Perkin Elmer) and 5 µL Reaction Buffer plus Activation Buffer mix containing AlphaScreen Acceptor beads was added. Plates were sealed with TopSeal-A adhesive film, gently agitated on a plate shaker for 2 h at room temperature. Afterwards 2 µL Dilution buffer with AlphaScreen Donor beads were added under subdued light and plates were sealed again with TopSeal-A adhesive film and covered with foil. Incubation takes place for further 2 h gently agitation at room temperature. Plates were then measured in an EnVision reader (Perkin Elmer) with the AlphaScreen program. Each data point (compound dilution) was measured as triplicate.

The $IC_{50}$ values were determined by means of a 4-parameter fit.

It will be apparent to persons skilled in the art that assays for other MKNK-1 kinases may be performed in analogy using the appropriate reagents.

Thus the compounds of the present invention effectively inhibit one or more MKNK-1 kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:
1. A compound of general formula (I):

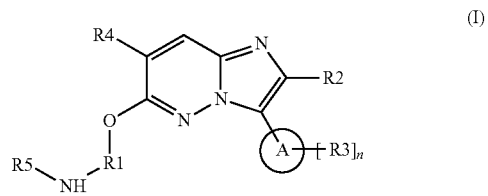

in which:

represents a:

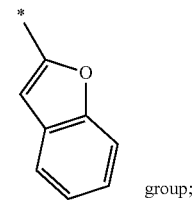

group;

wherein * indicates the point of attachment of said group with the rest of the molecule; and R1 represents a linear $C_1$-$C_6$-alkyl-, a branched $C_3$-$C_6$-alkyl-, or a $C_3$-$C_6$-cycloalkyl group which is optionally substituted, one or more times, independently from each other, with a substituent selected from:

a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R" group;

R2 represents a hydrogen atom;
R3 represents a substituent selected from:
a halogen atom, a —CN, $C_1$-$C_6$-alkyl-, $C_1$-$C_6$-haloalkyl-, $C_2$-$C_6$-alkenyl-, $C_2$-$C_6$-alkynyl-, —C(=O)R', —C(=O)NH$_2$, —C(=O)N(H)R', —C(=O)N(R')R", —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group;

R4 represents a substituent selected from:
a hydrogen atom, a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl-optionally substituted one or more times, independently from each other, with an R substituent; heteroaryl- optionally substituted one or more times, independently from each other, with an R substituent; —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R" group;

R represents a substituent selected from:
a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl-, heteroaryl-, —C(=O)R', —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R"group;

R' and R" represent, independently from each other, a substituent selected from:
a $C_1$-$C_6$-alkyl-, $C_3$-$C_{10}$-cycloalkyl-, $C_1$-$C_6$-haloalkyl group;

R5 represents:
either:
a substituent selected from a $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, $C_3$-$C_{10}$-cycloalkyl-$C_1$-$C_6$-alkyl-, aryl-, —C(=O)NH$_2$, —C(=O)N(H)R', —C(=O)N(R')R", —S(=O)R', —S(=O)$_2$R' group;
or:
together, with the nitrogen atom to which it is bound, and with a carbon atom of R1, form a 3- to 7-membered cyclic secondary amine group, which is optionally substituted with a substituent selected from:
a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$ alkyl-S—, —S(=O)R', —S(=O)$_2$R', —S(=O)$_2$NH$_2$, —S(=O)$_2$NHR', —S(=O)$_2$N(R')R" group;

n represents an integer of 0, 1, 2, 3, 4 or 5;
or a stereoisomer, a tautomer, or a salt thereof, or a mixture of same.

2. The compound according to claim 1, wherein:

represents a:

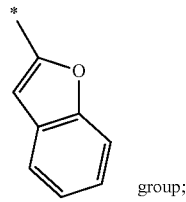

group;

wherein * indicates the point of attachment of said group with the rest of the molecule; and R1 represents a linear $C_1$-$C_6$-alkyl-, a branched $C_3$-$C_6$-alkyl-, or a $C_3$-$C_6$-cycloalkyl group which is optionally substituted, one or more times, independently from each other, with a substituent selected from:
a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, aryl-, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R" group;

R2 represents a hydrogen atom;
R3 represents a substituent selected from:
a halogen atom, a —CN, $C_1$-$C_6$-alkyl-, $C_1$-$C_6$-haloalkyl-, —OH, $C_1$-$C_6$-alkoxy-, $C_1$-$C_6$-haloalkoxy-group;
R4 represents a substituent selected from:
a hydrogen atom, a halogen atom, a —CN, $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-cycloalkyl-, 3- to 10-membered heterocycloalkyl-, aryl-optionally substituted one or more times, independently from each other, with an R substituent; heteroaryl- optionally substituted one or more times, independently from each other, with an R substituent; —C(=O)NH$_2$, —C(=O)N(H)R', —C(=O)N(R')R", —C(=O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, $C_1$-$C_6$-alkoxy-, $C_1$-$C_6$-haloalkoxy-, —OC(=O)R', —OC(=O)NH$_2$, —OC(=O)NHR', —OC(=O)N(R')R", —SH, $C_1$-$C_6$-alkyl-S—, —S(=O)R', —S(=O)₂R', —S(=O)₂NH₂, —S(=O)₂NHR', —S(=O)₂N(R')R", —(=O)(=NR') R" group;

R represents a substituent selected from:
a halogen atom, a —CN, C₁-C₆-alkyl-, C₁-C₆-haloalkyl-, C₂-C₆-alkenyl-, C₂-C₆-alkynyl-, C₃-C₁₀-cycloalkyl-, 3- to 10-membered heterocycloalkyl-, aryl-, heteroaryl-, —C(=O)R', —C(=O)NH₂, —C(=O)N(H)R', —C(=O)N(R')R", —C(=O)OR', —NH₂, —NHR', —N(R')R", —N(H)C(=O)R', —N(R')C(=O)R', —N(H)C(=O)NH₂, —N(H)C(=O)NHR', —N(H)C(=O)N(R')R", —N(R')C(=O)NH₂, —N(R')C(=O)NHR', —N(R')C(=O)N(R')R", —N(H)C(=O)OR', —N(R')C(=O)OR', —NO₂, —N(H)S(=O)R', —N(R')S(=O)R', —N(H)S(=O)₂R', —N(R')S(=O)₂R', —N=S(=O)(R')R", —OH, C₁-C₆-alkoxy-, C₁-C₆-haloalkoxy-, —OC(=O)R', —OC(=O)NH₂, —OC(=O)NHR', —OC(=O)N(R')R", —SH, C₁-C₆-alkyl-S—, —S(=O)R', —S(=O)₂R', —S(=O)₂NH₂, —S(=O)₂NHR', —S(=O)₂N(R')R", —S(=O)(=NR')R"group;

R' and R" represent, independently from each other, a substituent selected from:
a C₁-C₆-alkyl-, C₃-C₁₀-cycloalkyl-, C₁-C₆-haloalkyl group;

R5 represents:
either:
a substituent selected from a C₁-C₆-alkyl-, C₁-C₆-haloalkyl-, C₂-C₆-alkenyl-, C₂-C₆-alkynyl-, C₃-C₁₀-cycloalkyl-, C₃-C₁₀-cycloalkyl-C₁-C₆-alkyl-, aryl-, —C(=O)NH₂, —C(=O)N(H)R', —C(=O)N(R')R", —S(=O)R', —S(=O)₂R' group;

or:
together, with the nitrogen atom to which it is bound and with a carbon atom of R1, form a 3- to 7-membered cyclic secondary amine group, which is optionally substituted with a substituent selected from:
a halogen atom, a —CN, C₁-C₆-alkyl-, C₁-C₆-haloalkyl-, C₂-C₆-alkenyl-, C₂-C₆-alkynyl-, C₃-C₁₀-cycloalkyl-, aryl-, —C(=O)NH₂, —C(=O)N(H)R', —C(=O)N(R')R", —C(=O)OH, —C(=O)OR', —NH₂, —NHR', —N(R')R", —N(H)C(=O)R', —N(R')C(=O)R', —N(H)S(=O)R', —N(R')S(=O)R', —N(H)S(=O)₂R', —N(R')S(=O)₂R', —N=S(=O)(R')R", —OH, C₁-C₆-alkoxy-, C₁-C₆-haloalkoxy-, —OC(=O)R', —OC(=O)NH₂, —OC(=O)NHR', —OC(=O)N(R')R", —SH, C₁-C₆ alkyl-S—, —S(=O)R', —S(=O)₂R', —S(=O)₂NH₂, —S(=O)₂NHR', —S(=O)₂N(R')R" group;

n represents an integer of 0, 1, 2, 3, 4 or 5;
or a stereoisomer, a tautomer, or a mixture of same.

3. The compound according to claim 1, wherein:

represents a:

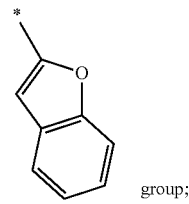
group;

wherein * indicates the point of attachment of said group with the rest of the molecule; and R1 represents a linear C₁-C₆-alkyl-, a branched C₃-C₆-alkyl-, or a C₃-C₆-cycloalkyl group which is optionally substituted, one or more times, independently from each other, with a substituent selected from:
a halogen atom, a —CN, C₁-C₆-alkyl-, C₁-C₆-haloalkyl-, C₂-C₆-alkenyl-, C₂-C₆-alkynyl-, C₃-C₁₀-cycloalkyl-, aryl-, —C(=O)NH₂, —C(=O)N(H)R', —C(=O)N(R')R", —C(=O)OH, —C(=O)OR', —NH₂, —NHR', —N(R')R", —N(H)C(=O)R', —N(R')C(=O)R', —N(H)S(=O)R', —N(R')S(=O)R', —N(H)S(=O)₂R', —N(R')S(=O)₂R', —N=S(=O)(R')R", —OH, C₁-C₆-alkoxy-, C₁-C₆-haloalkoxy-, —OC(=O)R', —OC(=O)NH₂, —OC(=O)NHR', —OC(=O)N(R')R", —SH, C₁-C₆-alkyl-S—, —S(=O)R', —S(=O)₂R', —S(=O)₂NH₂, —S(=O)₂NHR', —S(=O)₂N(R')R" group;

R2 represents a hydrogen atom;
R3 represents a substituent selected from:
a halogen atom, a —CN, C₁-C₆-alkyl-, C₁-C₆-haloalkyl-, —OH, C₁-C₆-alkoxy-, C₁-C₆-haloalkoxy-group;
R4 represents a substituent selected from:
a hydrogen atom, a halogen atom, a —CN, C₁-C₆-alkyl-, C₁-C₆-haloalkyl, C₃-C₁₀-cycloalkyl-, aryl-, heteroaryl-group;

R' and R" represent, independently from each other, a substituent selected from:
a C₁-C₆-alkyl-, C₃-C₁₀-cycloalkyl-, C₁-C₆-haloalkyl group;

R5 represents:
either:
a substituent selected from a C₁-C₆-alkyl-, C₁-C₆-haloalkyl-, C₂-C₆-alkenyl-, C₂-C₆-alkynyl-, C₃-C₁₀-cycloalkyl-, C₃-C₁₀-cycloalkyl-C₁-C₆-alkyl-, aryl-, —C(=O)NH₂, —C(=O)N(H)R', —C(=O)N(R')R", —S(=O)R', —S(=O)₂R' group;

or:
together, with the nitrogen atom to which it is bound and with a carbon atom of R1, form a 3- to 7-membered cyclic secondary amine group;

n represents an integer of 0 or 1;
or a stereoisomer, a tautomer, or a salt thereof, or a mixture of same.

4. The compound according to claim 1, wherein:

represents a:

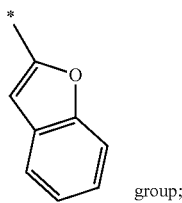

group;

wherein * indicates the point of attachment of said group with the rest of the molecule; and R1 represents a linear $C_1$-$C_5$-alkyl-, a branched $C_3$-$C_5$-alkyl-, or a $C_4$-$C_6$-cycloalkyl group which is optionally substituted, one or more times, independently from each other, with a substituent selected from:

a $C_1$-$C_6$-alkyl- or an aryl-group;

R2 represents a hydrogen atom;

R3 represents a substituent selected from:

a halogen atom, a —CN, $C_1$-$C_6$-alkyl-, $C_1$-$C_6$-haloalkyl-, —OH, $C_1$-$C_6$-alkoxy-, $C_1$-$C_6$-haloalkoxy-group;

R4 represents a substituent selected from:

a hydrogen atom, a halogen atom, a —CN, $C_1$-$C_6$-alkyl-, $C_1$-$C_6$-haloalkyl, $C_3$-$C_{10}$-cycloalkyl-, aryl-, heteroaryl-group;

R' and R" represent, independently from each other, a substituent selected from:

a $C_1$-$C_6$-alkyl-, $C_3$-$C_{10}$-cycloalkyl-, $C_1$-$C_6$-haloalkyl group;

R5 represents:

either:

a substituent selected from a $C_1$-$C_6$-alkyl-, $C_1$-$C_6$-haloalkyl-, $C_2$-$C_6$-alkenyl-, $C_2$-$C_6$-alkynyl-, $C_3$-$C_{10}$-alkyl-, $C_3$-$C_{10}$-cycloalkyl-$C_1$-$C_6$-alkyl-, aryl-, —C(=O)NH$_2$, —C(=O)N(H)R', —C(=O)N(R')R", —S(=O)R', —S(=O)$_2$R' group;

or:

together, with the nitrogen atom to which it is bound and with a carbon atom of R1, form a 3- to 7-membered cyclic secondary amine group;

n represents an integer of 0 or 1;

or a stereoisomer, a tautomer, or a salt thereof, or a mixture of same.

5. The compound according to claim 1, wherein:

represents a:

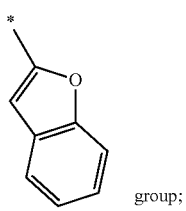

group;

wherein * indicates the point of attachment of said group with the rest of the molecule; and R1 represents a linear $C_1$-$C_5$-alkyl-group which is optionally substituted, once with a substituent which is:

an aryl-group;

R2 represents a hydrogen atom;

R3 represents a substituent selected from:

a halogen atom, a $C_1$-$C_6$-alkoxy-group;

R4 represents a hydrogen atom;

R5 represents:

either:

a substituent selected from a $C_1$-$C_6$-alkyl-, $C_3$-$C_{10}$-cycloalkyl-, $C_3$-$C_{10}$-cycloalkyl-$C_1$-$C_6$-alkyl-group;

or:

together, with the nitrogen atom to which it is bound and with a carbon atom of R1, form a 3- to 7-membered cyclic secondary amine group;

n represents an integer of 0 or 1;

or a stereoisomer, a tautomer, or a salt thereof, or a mixture of same.

6. The compound according to claim 1, which is selected from the group consisting of:

3-(1-Benzofuran-2-yl)-6-[2-(morpholin-2-yl)ethoxy]imidazo[1,2-b]pyridazine;

3-(4-Methoxy-1-benzofuran-2-yl)-6-[(2R)-morpholin-2-ylmethoxy]imidazo[1,2-b]pyridazine;

3-(1-Benzofuran-2-yl)-6-(morpholin-2-ylmethoxy)imidazo[1,2-b]pyridazine;

N-(3-{[3-(1-Benzofuran-2-yl)imidazo[1,2-b]pyridazin-6-yl]oxy}propyl)-2,2-dimethylpropan-1-amine;

3-(5-Methoxy-1-benzofuran-2-yl)-6-[(2R)-morpholin-2-ylmethoxy]imidazo[1,2-b]pyridazine;

2-{[3-(1-Benzofuran-2-yl)imidazo[1,2-b]pyridazin-6-yl]oxy}-N-(cyclopropylmethyl)ethanamine;

3-(1-Benzofuran-2-yl)-6-[(2R)-morpholin-2-ylmethoxy]imidazo[1,2-b]pyridazine;

3-(1-Benzofuran-2-yl)-6-{2-[(3R)-morpholin-3-yl]ethoxy}imidazo[1,2-b]pyridazine;

3-{[3-(1-Benzofuran-2-yl)imidazo[1,2-b]pyridazin-6-yl]oxy}-N-(propan-2-yl)propan-1-amine;

N-(2-{[3-(1-Benzofuran-2-yl)imidazo[1,2-b]pyridazin-6-yl]oxy}ethyl)propan-2-amine;

3-(1-Benzofuran-2-yl)-6-[(2S)-morpholin-2-ylmethoxy]imidazo[1,2-b]pyridazine;

N-(2-{[3-(1-Benzofuran-2-yl)imidazo[1,2-b]pyridazin-6-yl]oxy}ethyl)-2,2-dimethylpropan-1-amine;

3-(1-Benzofuran-2-yl)-6-{2-[(3S)-morpholin-3-yl]ethoxy}imidazo[1,2-b]pyridazine;

6-(Azetidin-3-ylmethoxy)-3-(1-benzofuran-2-yl)imidazo[1,2-b]pyridazine;

3-(1-Benzofuran-2-yl)-6-{2-[(2S)-pyrrolidin-2-yl]ethoxy}imidazo[1,2-b]pyridazine;

3-(1-Benzofuran-2-yl)-6-(piperidin-2-ylmethoxy)imidazo[1,2-b]pyridazine;

N-(2-{[3-(1-Benzofuran-2-yl)imidazo[1,2-b]pyridazin-6-yl]oxy}ethyl)cyclopropanamine;

N-(2-{[3-(1-Benzofuran-2-yl)imidazo[1,2-b]pyridazin-6-yl]oxy}ethyl)-2-methylpropan-2-amine;

2-{[3-(1-Benzofuran-2-yl)imidazo[1,2-b]pyridazin-6-yl]oxy}-N-(propan-2-yl)propan-1-amine;

3-(5-Chloro-1-benzofuran-2-yl)-6-[(2R)-morpholin-2-ylmethoxy]imidazo[1,2-b]pyridazine;

3-(1-Benzofuran-2-yl)-6-[(2R)-pyrrolidin-2-ylmethoxy]imidazo[1,2-b]pyridazine;

3-(1-Benzofuran-2-yl)-6-(piperidin-3-yloxy)imidazo[1,2-b]pyridazine;

3-(1-Benzofuran-2-yl)-6-[(2S)-pyrrolidin-2-ylmethoxy]imidazo[1,2-b]pyridazine;

1{[3-(1-Benzofuran-2-yl)imidazo[1,2-b]pyridazin-6-yl]oxy}-N-methylpropan-2-amine;
3-(5-Chloro-1-benzofuran-2-yl)-6-{2-[(2S)-pyrrolidin-2-yl]ethoxy}imidazo[1,2-b]pyridazine;
2-{[3-(1-Benzofuran-2-yl)imidazo[1,2-b]pyridazin-6-yl]oxy}-N-methylpropan-1-amine;
Formic acid-N-(2-{[3-(1-benzofuran-2-yl)imidazo[1,2-b]pyridazin-6-yl]oxy}-2-phenylethyl)propan-2-amine (1:1);
N-(2-{[3-(1-Benzofuran-2-yl)imidazo[1,2-b]pyridazin-6-yl]oxy}-2-phenylethyl)-2-methylpropan-1-amine;
(-)-2-{[3-(1-Benzofuran-2-yl)imidazo[1,2-b]pyridazin-6-yl]oxy}-N-methyl-2-phenylethanamine;
N-(2-{[3-(1-Benzofuran-2-yl)imidazo[1,2-b]pyridazin-6-yl]oxy}-2-phenylethyl)-2,2-dimethylpropan-1-amine;
3-(1-benzofuran-2-yl)-6-[(3R)-pyrrolidin-3-yloxy]imidazo[1,2-b]pyridazine;
3-(1-benzofuran-2-yl)-6-[(3R)-piperidin-3-yloxy]imidazo[1,2-b]pyridazine;
3-(4-fluoro-1-benzofuran-2-yl)-6-[(2R)-morpholin-2-yl-methoxy]imidazo[1,2-b]-pyridazine;
3-(5-fluoro-1-benzofuran-2-yl)-6-[(2R)-morpholin-2-yl-methoxy]imidazo[1,2-b]-pyridazine;
a streoisomer thereof;
a tautomer thereof;
a salt thereof; and
a mixture thereof.

7. A method of preparing a compound according to claim 1, comprising reacting an intermediate compound of general formula (V):

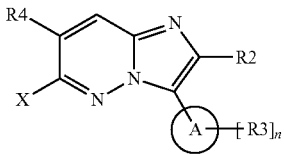
(V)

in which A, R2, R3, R4 and n are as defined in claim 1, and X represents a leaving group, with a compound of general formula (III):

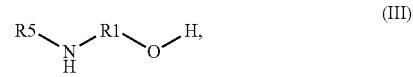
(III)

in which R1 and R5 are defined in claim 1,
thereby giving a compound of general formula (I):

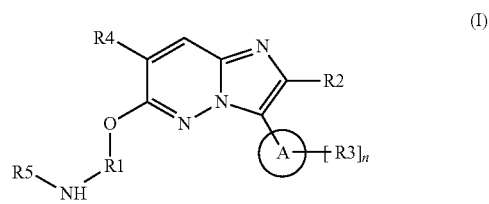
(I)

in which A, R1, R2, R3, R4, R5 and n are as defined in claim 1.

8. A pharmaceutical composition comprising a compound of general formula (I), or a stereoisomer, a tautomer, or a pharmaceutically acceptable salt thereof, or a mixture of same, according to claim 1, and a pharmaceutically acceptable diluent or carrier.

9. A pharmaceutical combination comprising:
one or more first active ingredients selected from compounds of general formula (I) according to claim 1, and
one or more second active ingredients selected from chemotherapeutic anti-cancer agents.

* * * * *